United States Patent
Silver et al.

(10) Patent No.: US 11,510,917 B2
(45) Date of Patent: Nov. 29, 2022

(54) HIF-STABILIZATION AND PREVENTION OF HYPEROXIA-INDUCED NEONATAL LUNG DISEASE

(71) Applicant: CORNELL UNIVERSITY, Ithaca, NY (US)

(72) Inventors: Randi B. Silver, New York, NY (US); Stefan Worgall, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/999,672

(22) PCT Filed: Feb. 17, 2017

(86) PCT No.: PCT/US2017/018283
§ 371 (c)(1),
(2) Date: Aug. 20, 2018

(87) PCT Pub. No.: WO2017/143131
PCT Pub. Date: Aug. 24, 2017

(65) Prior Publication Data
US 2019/0298709 A1 Oct. 3, 2019

Related U.S. Application Data

(60) Provisional application No. 62/297,508, filed on Feb. 19, 2016.

(51) Int. Cl.
| A61K 31/472 | (2006.01) |
| A61P 11/00 | (2006.01) |
| A61K 31/197 | (2006.01) |
| A61K 31/47 | (2006.01) |
| A61K 31/4418 | (2006.01) |
| A61K 31/4709 | (2006.01) |

(52) U.S. Cl.
CPC .......... *A61K 31/472* (2013.01); *A61K 31/197* (2013.01); *A61K 31/4418* (2013.01); *A61K 31/47* (2013.01); *A61K 31/4709* (2013.01); *A61P 11/00* (2018.01)

(58) Field of Classification Search
CPC ................ A61K 31/472; A61K 31/197; A61K 31/4418; A61K 31/47; A61K 31/4709; A61P 11/00
See application file for complete search history.

(56) References Cited

U.S. PATENT DOCUMENTS

| 2012/0121720 A1 | 5/2012 | Stamler et al. |
| 2013/0245037 A1 | 9/2013 | Guenzler-Pukall et al. |
| 2015/0322015 A1 | 11/2015 | Witschi et al. |

FOREIGN PATENT DOCUMENTS

| WO | WO-02086497 A2 * | 10/2002 | ......... A61K 38/1866 |
| WO | 2015095757 A1 | 6/2015 | |
| WO | WO-2015095757 A1 * | 6/2015 | ........... A61K 31/472 |

OTHER PUBLICATIONS

International Search Report dated May 4, 2017 issued in PCT/US2017/018283.
Hoppe G. et al., "Comparative systems pharmacology of HIF stabilization in the prevention of retinopathy of prematurity", PNAS (Apr. 2016), vol. 113, No. 18, 10 pages.
Sears J.E. et al., "Prolyl hydroxylase inhibition during hyperoxia prevents oxygen-induced retinopathy", PNAS (Dec. 2008), vol. 105, No. 50, pp. 19898-19903.
Asikainen T.M. et al., "Enhancement of angiogenic effectors through hypoxia-inducible factor in preterm primate lung in vivo", Am J Physiol Lung Cell Mol Physiol (May 2006), vol. 291, pp. L588-L595.
Shimoda L.A. et al., "HIF and the Lung: Role of Hypoxia-inducible Factors in Pulmonary Development and Disease", American Journal of Respiratory and Critical Care Medicine (2011), vol. 183, pp. 152-156.
Trichonas G. et al., "Prolyl Hydroxylase Inhibition During Hyperoxia Prevents Oxygen-Induced Retinopathy in the Rat 50/10 Model", Investigative Opthalmology & Visual Science (Jul. 2013), vol. 54, No. 7, pp. 4919-4926.
Asikainen T.M. et al., "Improved lung growth and function through hypoxiainducible factor in primate chronic lung disease of prematurity", The FASEB Journal (2006), vol. 20, pp. 1698-1700.
Velten M. et al., "Deficits in lung alveolarization and function after systemic maternal inflammation and neonatal hyperoxia exposure", Journal of Applied Physiology (May 2010), vol. 108, pp. 1347-1356.

(Continued)

*Primary Examiner* — James D. Anderson
*Assistant Examiner* — William Y Lee
(74) *Attorney, Agent, or Firm* — Scully, Scott, Murphy & Presser, P.C.

(57) ABSTRACT

The disclosure provides a method comprising administering HIF stabilizing small molecule drugs to premature infants, whose survival is dependent upon mechanical ventilation and/or supplemental oxygen, to counteract the pathological effects of hyperoxia on lung development. Data in a mouse model of hyperoxia-induced neonatal lung disease supports a treatment with a HIF stabilizer during high oxygen exposure protects the lung. HIF stabilizers can be administered via various routes, including in an aerosolized state using a ventilator, intravenous, intraperitoneal or subcutaneous injection.

11 Claims, 13 Drawing Sheets
Specification includes a Sequence Listing.

(56) References Cited

OTHER PUBLICATIONS

Wang H. et al., "Severity of neonatal hyperoxia determines structural and functional changes in developing mouse airway", American Journal of Physiology—Lung Cellular and Molecular Physiology (2014), vol. 307, No. 4, pp. L295-L301.
Park A.M. et al., "Hypoxia-inducible factor (HIF) and HIF-stabilizing agents in neonatal care" Semin Fetal Neonatal Med (Aug. 2010), vol. 15, No. 4, 14 pages.
Maxwell, P. H., et al.,"HIF prolyl hydroxylase inhibitors for the treatment of renal anaemia and beyond Nature Reviews", Nephrology, Mar. 2016, pp. 157-168, 12.3.

* cited by examiner

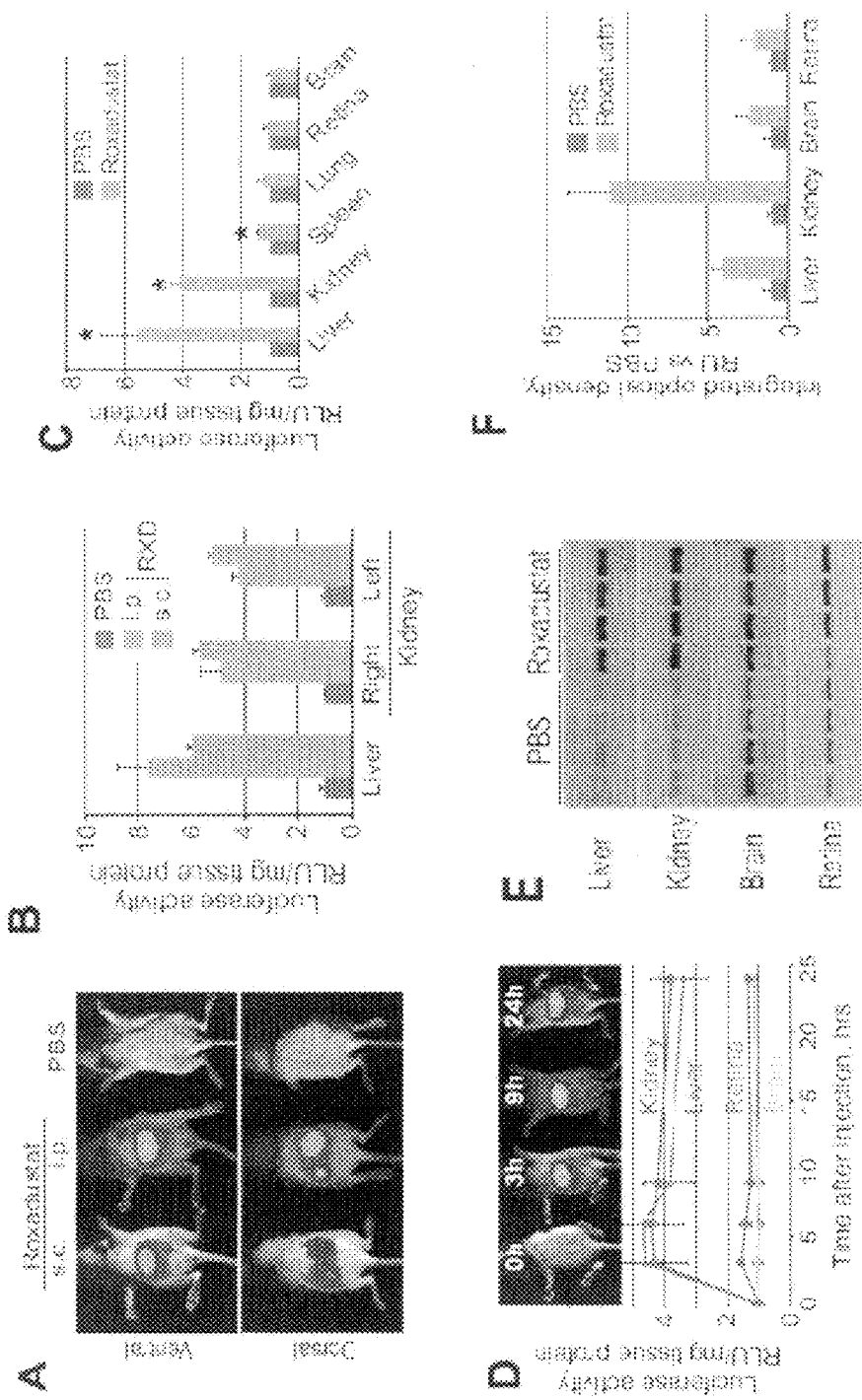
Figure 3A-F

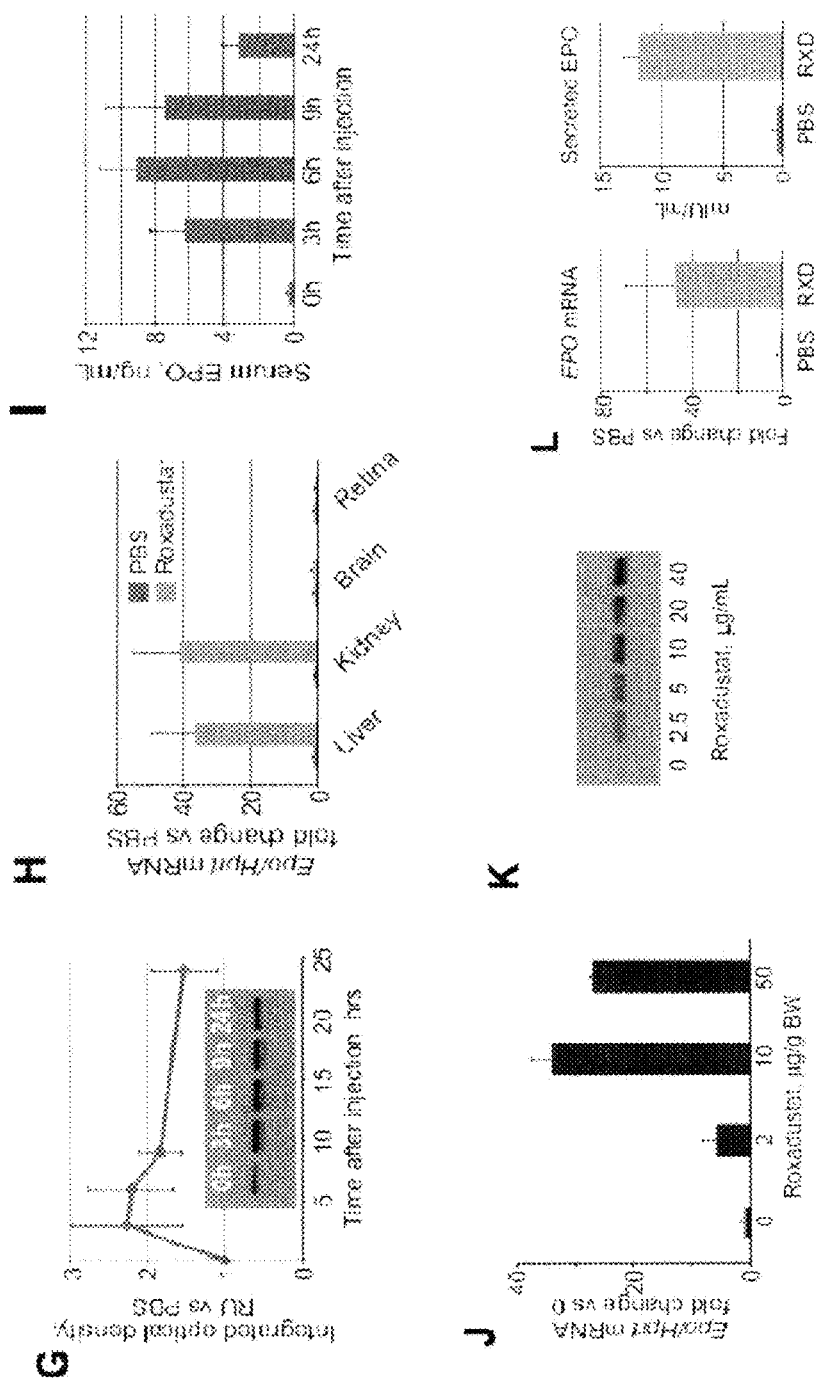
Figure 3G-L

HIF-STABILIZATION AND PREVENTION OF HYPEROXIA-INDUCED NEONATAL LUNG DISEASE

CROSS REFERENCE TO RELATED APPLICATION

This application claims the benefit of priority from U.S. Provisional Application No. 62/297,508, filed Feb. 19, 2016, the entire contents of which are incorporated herein by reference.

INCORPORATION BY REFERENCE OF SEQUENCE LISTING

The Sequence Listing in an ASCII text file, 33183_7305_03_US_Sequence_Listing.txt of 4 KB, created on Aug. 16, 2018, and submitted to the United States Patent and Trademark Office via EFS-Web, is incorporated herein by reference.

BACKGROUND

One in eight children in the United States is born prematurely, which amounts to about half a million babies born prematurely each year. Oxygen supplementation, a necessary life sustaining measure in premature birth, can permanently adversely affect the lung, an organ that requires complete gestation for development. Severely premature infants commonly rely on mechanical ventilation and supplemental oxygen for survival. Unfortunately, high oxygen is toxic to many organs (including the lung) which leads to chronic lung disease and difficulty breathing. Of the half a million prematurely born babies in the US, about 60,000 of them (who are also below 1500 grams in birth weight) are at high risk for developing Chronic Lung Disease of prematurity.

Chronic lung disease of prematurity (CLD) (a.k.a. bronchopulmonary dysplasia or BPD), characterized by arrested alveolar development and impaired lung function later in life, is clearly associated with neonatal oxygen supplementation. Additionally, premature birth and CLD may predispose the baby for the development of asthma and chronic obstructive pulmonary disease (COPD) later in life. Impaired alveolarization, scarring and inflammation are hallmarks of CLD. There are currently no effective treatment strategies to prevent CLD. CLD treatment in the US costs an estimated 2.4 billion annually, which is the second most expensive disease only behind the cost of treating asthma.

Increasing evidence suggests that angiogenesis and alveolar growth are intricately coupled, and impaired vascular development disrupts alveolar development. Hyperoxia (high oxygen) is known to regulate a variety of transcription factors. Hypoxia inducible factor (HIF-1) is an oxygen-dependent transcription factor that is a known key player in the coordinated processes of angiogenesis, inflammation and tissue growth during normal tissue development.

HIF-1 is a heterodimer composed of 2 subunits, HIF-1α and HIF-1β. HIF-1β is constitutively expressed and its mRNA and protein are maintained at constant levels regardless of oxygen availability. HIF-1α protein is highly regulated by oxygen and is rapidly degraded. The stability of HIF-1α is regulated principally through hydroxylation of proline residues by prolyl hydroxylase domain-containing proteins (PHDs). In hyperoxia the HIF PHDs are activated causing the breakdown of HIF-1α.

There are multiple examples of HIF PHD antagonists that function as competitive inhibitors. These inhibitors can act as competitive antagonist of 2-oxoglutarate, a cofactor that accepts one oxygen from molecular dioxygen to become succinate as the second oxygen forms trans-4-hydroxyproline. Although the most basic structure of HIF PHD antagonists is found in dimethyloxalylglycine (DMOG), hydrazones, carboxamides, and quinolones have been established as potent HIF stabilizers.

Mast cells are a type of white blood cells derived from myeloid stem cells. They are part of the immune and neuroimmune systems and contain many granules rich in histamine and heparin. Prior to birth, mast cell progenitors from the bone marrow enter the circulation. These precursors enter vascularized tissues where the precursors mature to mast cells, expressing mast cell phenotype under the influence of stem cell factor and other locally produced cytokines.

Although best known for a role in allergy and anaphylaxis, mast cells play an important role in inflammation, fibrosis, wound healing, angiogenesis, immune tolerance, defense against pathogens, and bloodbrain barrier function. Mast cells possess plasticity—their phenotype is heterogeneous in that they develop into distinct populations dictated by local signals from their milieu.

BRIEF DESCRIPTION OF THE DRAWINGS

FIGS. 3A-3L. Roxadustat targets liver and kidney. (A) Both intraperitoneal (i.p.) and subcutaneous (s.c.) injection create liver and kidney specific luminescence in the luciferase-oxygen dependent degradation domain (luc-ODD) mouse. (B) Quantification of luciferase activity in organ lysates demonstrates liver and kidney tropism by either i.p. or s.c. injection of Roxadustat (RXD). (C) Luminescence of organ lysates of i.p. Roxadustat indicates specificity for liver and kidney, $*p<5\times10^{-4}$. (D) Time duration of hypoxia inducible factor prolyl hydroxylase inhibition by Roxadustat gives sustained stabilization of luc-ODD over 24 hours. (E) Western blot analysis of HIF-1α protein after Roxadustat. (F) Integrated optical density of immunoblot analysis in FIG. 3E. (G) Densitometry of HIF-1α immunoblot (insert) over time after Roxadustat i.p. injection. (H) Epo mRNA expression in organs after Roxadustat i.p. injection. (I) Serum EPO concentration versus time after i.p. Roxadustat. (J) Dose-dependent expression of Epo mRNA in the liver. (K) Dose response of HIF-1α to Roxadustat in cultured Hep3B cells analyzed by Western blotting. (L) EPO mRNA levels in cultured Hep3B cells and EPO protein content on Hep3B culture media in response to Roxadustat.

DETAILED DESCRIPTION OF THE INVENTION

Figure 1:
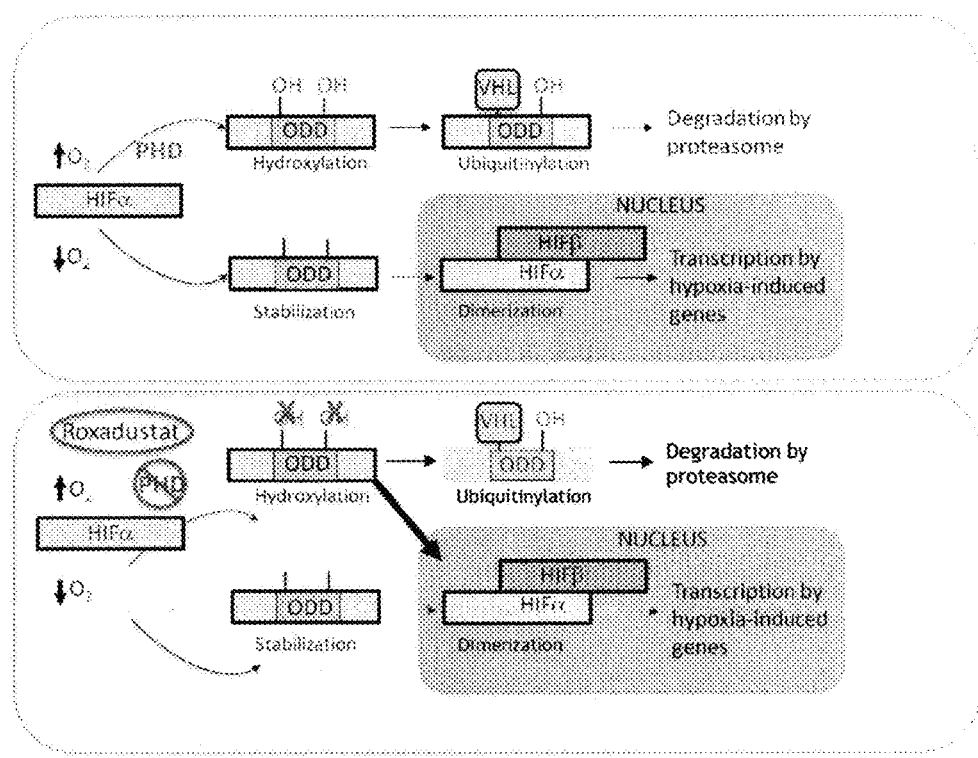
FIG. 1. A model of action of HIF catabolism and effect of PHD inhibitors. Top panel—Oxygen activates hypoxia inducible factor prolyl hydroxylase (PHD) to induce catabolism of HIFα. Bottom panel—Inhibition of PHD with roxadustat can stabilize HIFα even in hyperoxia.

Premature birth is associated with bronchopulmonary dysplasia also referred to as neonatal chronic lung disease of prematurity (CLD). CLD is linked to long-term abnormalities in lung function and mechanics CLD persists into adolescence and young adulthood manifesting as an asthma-like phenotype and possibly predisposing to chronic obstructive pulmonary disease (COPD) later in life. The causes of CLD are unknown but it is thought to result from inflammation-mediated injury that is modified by maternal and postnatal exposures, particularly supplemental oxygen. As inflammation is central to the development of CLD, inflammatory cells, including mast cells, are prominent in the lungs of preterm infants. Genome wide transcriptional profiling confirmed that three of the five most highly induced genes in CLD are mast cell markers. Accumulation of tryptase-positive mast cells in autopsy specimen obtained from infants with CLD were first described twenty years ago. Despite evidence of their presence in CLD the pathophysiological contribution of mast cells is virtually unknown. There is an urgent need to correct this gap in knowledge because, until this is accomplished, the prevention and treatment of at-risk premature newborns for CLD will likely remain beyond our reach.

Increasing evidence suggests that angiogenesis and alveolar growth are intricately coupled, and impaired vascular development disrupts alveolarization. Hyperoxia is known to regulate a variety of transcription factors that alter angiogenesis and lung vascularization in models of CLD. HIF-1 is an oxygen-dependent transcription factor and is a key player in the coordinated processes of angiogenesis, inflammation and tissue growth during normal tissue development. Hyperoxia inhibits HIF-1 and thereby alters lung vascularization, inflammation and tissue growth. HIF-1 is a heterodimer composed of 2 subunits, HIF-1α and HIF-1β. HIF-1β is constitutively expressed and its mRNA and protein are maintained at constant levels regardless of oxygen availability. HIF-1α protein is highly regulated by oxygen and in normoxia, the HIF-1α proteins are rapidly degraded. The stability of HIF-1α is regulated principally through hydroxylation of proline residues by prolyl hydroxylase domain-containing proteins (PHDs). HIF PHDs are activated in hyperoxia and cause the breakdown of HIF-1α.

The present invention is predicated at least in part on modulating the HIF pathway for therapeutic purposes in the prevention, amelioration and/or attenuation of CLD. The strategy disclosed herein is to pharmacologically override the hyperoxia-induced breakdown of HIF-1α by stabilizing PHDs.

The term "prevention" used herein means delay or eliminate the onset of CLD during oxygen supplementation, or reduce the occurrences of CLD during oxygen supplementation among a population of patients.

The onset of CLD can be determined by examining the bronchoalveolar lavage fluid (BAL) from a subject. Bronchoalveolar lavage (informally, "bronchoalveolar washing") is a medical procedure in which a bronchoscope is passed through the mouth or nose into the lungs and fluid is squirted into a small part of the lung and then collected for examination.

In another embodiment tracheal aspirates from a ventilator supplementing oxygen to a premature neonate are examined to determine the onset of CLD.

In one embodiment BAL analysis is performed to diagnose lung disease as follows: BAL (or tracheal aspirate) is filtered and centrifuged. Cell debris-free BAL (or tracheal aspirate) fluid supernatants are used for analysis of β-hex, histamine, and elastase. Increases in BAL levels of β-hex, an index of mast cell degranulation, histamine and elastase indicate mast cell activity and CLD onset.

The term "preterm", as used herein, refers to a baby born less than 37 weeks gestational age. Babies born prematurely are also known as preemies or premmies.

In one embodiment, an effective amount of a small molecule HIF stabilizer is administered to a subject in need thereof. In a specific embodiment the subject in need of a HIF1 stabilizer treatment is a preterm neonatal (new born) baby, particularly a preterm baby undergoing oxygen supplementation, i.e., a preterm baby who is provided with supplemental oxygen.

The term "supplemental oxygen" herein refers to additional oxygen supplied to a subject in need thereof providing an oxygen concentration above the oxygen concentration in room air (RA). Room air is composed of about 21% oxygen. In some embodiments, the supplemented oxygen concentration is mild (mild hyperoxia, approximately 30% oxygen is provided), medium (moderate hyperoxia, approximately 45% oxygen is provided), or high (severe hyperoxia, approximately 80% oxygen is provided).

The term "blood oxygen saturation", as used herein, refers to the fraction of oxygen-saturated hemoglobin relative to total hemoglobin (unsaturated+saturated) in the blood. Blood oxygen saturation of a subject can be measured in various ways including with a pulse oximeter, with an arterial blood gas (ABG) analyzer, or with a CO-oximeter. Blood oxygen saturation can be used to determine the pattern and duration of oxygen supplementation. Supplemental oxygen can be administered to a subject when the blood oxygen saturation level of the subject is below 95%, e.g. when the blood oxygen saturation of the subject is 90%, 85%, or 80%.

In one embodiment, a HIF stabilizer is not administered to the subject continuously; rather it is administered intermittently. In a specific embodiment, intermittent HIF stabilizer administration is performed once every other day, every three days, every four days, every five days, or once a week. In another specific embodiment, intermittent HIF stabilizer administration is performed once every hour, every two hours, every three hours, every six hours, every ten hours, or every twelve hours. In another embodiment, a HIF stabilizer is administered only when supplemental oxygen is also administered. In a specific embodiment, supplementary oxygen and HIF stabilizer are administered based on low blood oxygen saturation levels, e.g., when the blood oxygen saturation of the subject is below 95%, 90%, 85%, or 80%. In yet another embodiment, a HIF stabilizer is administered until the subject is no longer in need for supplemental oxygen, i.e. when the subject can maintain a blood oxygen saturation level equal to or above 95% in room air.

In some embodiments, an effective amount of a HIF stabilizer is about 0.2 mg/kg to 100 mg/kg. In other embodiments, the effective amount of a HIF stabilizer is about 0.2 mg/kg, 0.5 mg/kg, 1 mg/kg, 8 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 150 mg/kg, 175 mg/kg or 200 mg/kg of HIF stabilizer.

In some embodiments, the HIF stabilizer is an agent that inhibits HIF hydroxylase activity. An agent that inhibits HIF hydroxylase activity is any agent that reduces or otherwise modulates the activity of a HIF hydroxylase enzyme.

In one embodiment, the HIF stabilizer is a small molecule compound that inhibits HIF hydroxylase activity. The term "small molecule compound" herein refers to small organic chemical compound, generally having a molecular weight of less than 2000 daltons, 1500 daltons, 1000 daltons, 800 daltons, or 600 daltons.

In particular embodiments of the present invention, the agent that inhibits HIF hydroxylase activity is a structural mimetic of 2-oxoglutarate. Such compounds may inhibit the target 2-oxoglutarate dioxygenase enzyme family member competitively.

The general structure of HIF hydroxylase inhibitors for use in this invention is

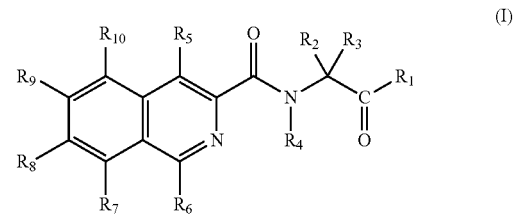

(I)

wherein:
R1 is selected from the group consisting of hydroxyl, alkoxy, substituted alkoxy, aryloxy, and substituted aryloxy;
R2 and R3 are independently selected from the group consisting of hydrogen, alkyl, substituted alkyl, cycloalkyl, substituted cycloalkyl, aryl, substituted aryl, heterocycloalkyl, substituted heterocycloalkyl, heteroaryl, and substituted heteroaryl; or R2 and R3 together with the carbon atom to which they are attached form a cycloalkyl, substituted cycloalkyl, hererocycloalkyl, or substituted hererocycloalkyl;

R4 is selected from the group consisting of hydrogen, alkyl, and substituted alkyl;

R5 is selected from the group consisting of hydroxyl, alkoxy, and substituted alkoxy;

R6 is selected from the group consisting of hydrogen, alkyl, substituted alkyl, cycloalkyl, substituted cycloalkyl, cyano, halo, hydroxyl, alkoxy, substituted alkoxy, amino, substituted amino, arylozy, substituted arylozy, aminoacyl, substituted aminoacyl, cycloalkoxy, substituted cycloalkoxy, aryl, substituted aryl, aryloxy, substituted aryloxy, heterocycloalkyl, substituted heterocycloalkyl, heteroaryloxy, substituted heteroaryloxy, heteroaryl, and substituted heteroaryl; and R7, R8, R9 and R10 are independently selected from the group consisting of hydrogen, halo, alkyl, substituted alkyl, cycloalkyl, substituted cycloalkyl, aryl, substituted aryl, heteroaryl, substituted heteroaryl, alkoxy, substituted alkoxy, aryloxy, and substituted aryloxy.

As used herein, the term "alkyl" refers to a straight or branched, saturated hydrocarbon group having 1 to 10 carbon atoms, more particularly from 1 to 5 carbon atoms, and even more particularly 1 to 3 carbon atoms. Representative alkyl groups include methyl, ethyl, n-propyl, iso-propyl, n-butyl, t-butyl, n-pentyl, and the like.

The term "substituted alkyl" refers to an alkyl group of from 1 to 10 carbon atoms, more particularly 1 to 5 carbon atoms, and having from 1 to 5 substituents, preferably 1 to 3 substituents, each of which substituents is independently selected from the group consisting of alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, thio, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, sulfonyl, substituted sulfonyl, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)2-alkyl, —OS(O)2-substituted alkyl, —OS(O)2-aryl, —OS(O)2-substituted aryl, —OS(O)2-heteroaryl, —OS(O)2-substituted heteroaryl, —OS(O)2-heterocyclic, —OS(O)2-substituted heterocyclic, and —OSO2-NR11R11, —NR11S(O)2-NR11-alkyl, —NR11S(O)2-NR11-substituted alkyl, —NR11S(O)2-NR11-aryl, —NR11S(O)2-NR11-substituted aryl, —NR11S(O)2-NR11-heteroaryl, —NR11S(O)2-NR11-substituted heteroaryl, —NR11S(O)2-NR11-heterocyclic, and —NR11S(O)2-NR11-substituted heterocyclic, wherein each R11 independently selected from hydrogen or alkyl. Representative substituted alkyl groups include trifluoromethyl, benzyl, pyrazol-1-ylmethyl and the like.

The term "alkoxy" refers to the group "alkyl-O—," which includes, by way of example, methoxy, ethoxy, n-propoxy, iso-propoxy, n-butoxy, t-butoxy, sec-butoxy, n-pentoxy, and the like.

The term "substituted alkoxy" refers to the group "substituted alkyl-O—".

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—, provided that a nitrogen atom of the heterocyclic or substituted heterocyclic is not bound to the —C(O)— group, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminoacyl" or "amide", or the prefix "carbamoyl," "carboxamide," "substituted carbamoyl" or "substituted carboxamide" refers to the group —C(O)NR12R12, wherein each R12 is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic; or wherein each R12 is joined to form together with the nitrogen atom a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "alkenyl" refers to a vinyl unsaturated monovalent hydrocarbyl group having from 2 to 6 carbon atoms, and preferably 2 to 4 carbon atoms, and having at least 1, and preferably from 1 to 2 sites of vinyl (>C=C<) unsaturation. Representative alkenyl groups include vinyl (ethen-1-yl), allyl, but-3-enyl and the like.

The term "substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This term includes both E (trans) and Z (cis) isomers as appropriate. It also includes mixtures of both E and Z components.

The term "alkynyl" refers to acetylenic unsaturated monovalent hydrocarbyl groups having from 2 to 6 carbon atoms, and preferably 2 to 3 carbon atoms, and having at least 1, and preferably from 1 to 2 sites of acetylenic (—C≡C—) unsaturation. Representative alkynyl groups include ethyn-1-yl, propyn-1-yl, propyn-2-yl, and the like.

The term "amino" refers to the group —NH2.

The term "substituted amino" refers to the group —NR13R13, wherein each R13 is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, sulfonyl, and substituted sulfonyl, provided that both R13 groups are not hydrogen; or the R13 groups can be joined together with the nitrogen atom to form a heterocyclic or substituted heterocyclic ring. Representative substituted amino groups include phenylamino, methylphenylamino, and the like. Representative substituted amino groups include (ethanic acid-2-yl)amino, and the like.

The term "acylamino" refers to the groups —NR14C(O) alkyl, —NR14C(O) substituted alkyl, —NR14C(O)cycloalkyl, —NR14C(O) substituted cycloalkyl, —NR14C(O)alkenyl, —NR14C(O) substituted alkenyl, —NR14C(O) alkynyl, —NR14C(O) substituted alkynyl, —NR14C(O) aryl, —NR14C(O) substituted aryl, —NR14C(O)heteroaryl, —NR14C(O) substituted heteroaryl, —NR14C(O)heterocyclic, and —NR14C(O) substituted heterocyclic, wherein R14 is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are defined herein.

The term "oxycarbonylamino" refers to the groups —NR15C(O)O-alkyl, —NR15C(O)O-substituted alkyl, —NR15C(O)O-alkenyl, —NR15C(O)O-substituted alkenyl, —NR15C(O)O-alkynyl, —NR15C(O)O-substituted alkynyl, —NR15C(O)O-cycloalkyl, —NR15C(O)O-substituted cycloalkyl, —NR15C(O)O-aryl, —NR15C(O)O-substituted aryl, —NR15C(O)O-heteroaryl, —NR15C(O)O-substituted heteroaryl, —NR15C(O)O-heterocyclic, and —NR15C(O)O-substituted heterocyclic, wherein R15 is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "oxythiocarbonylamino" refers to the groups —NR16C(S)O-alkyl, —NR16C(S)O-substituted alkyl, —NR16C(S)O-alkenyl, —NR16C(S)O-substituted alkenyl, —NR16C(S)O-alkynyl, —NR16C(S)O-substituted alkynyl, —NR16C(S)O-cycloalkyl, —NR16C(S)O-substituted cycloalkyl, —NR16C(S)O-aryl, —NR16C(S)O-substituted aryl, —NR16C(S)O-heteroaryl, —NR16C(S)O-substituted heteroaryl, —NR16C(S)O-heterocyclic, and —NR16C(S)O-substituted heterocyclic, wherein R16 is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonyloxy," or the prefix "carbamoyloxy" or "substituted carbamoyloxy," refers to the groups —OC(O)NR17R17, wherein each R17 is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic; or wherein each R17 is joined to form, together with the nitrogen atom, a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonylamino" refers to the group —NR18C(O)—NR18R18, herein each R18 is independently selected from the group consisting of hydrogen and alkyl.

The term "aminothiocarbonylamino" refers to the group —NR19C(S)—NR19R19, wherein each R19 is independently selected from the group consisting of hydrogen and alkyl.

The term "aryl" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is the aryl group. Preferred aryls include phenyl and naphthyl.

The term "substituted aryl" refers to aryl groups, as defined herein, which are substituted with from 1 to 4, particularly 1 to 3, substituents selected from the group consisting of hydroxyl, acyl, acylamino, acyloxy, alkyl, substituted alkyl, alkoxy, substituted alkoxy, alkenyl, substituted alkenyl, alkynyl, substituted alkynyl, amidino (—C(=NH)-amino or substituted amino), amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters, cyano, thio, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino (—NH—C(=NH)-amino or substituted amino), halo, nitro, heteroaryl, substituted heteroaryl, heterocyclic, substituted heterocyclic, oxycarbonylamino, oxythiocarbonylamino, sulfonyl, substituted sulfonyl, —OS(O)2-alkyl, —OS(O)2-substituted alkyl, —OS(O)2-aryl, —OS(O)2-substituted aryl, —OS(O)2-heteroaryl, —OS(O)2-substituted heteroaryl, —OS(O)2-heterocyclic, —OS(O)2-substituted heterocyclic, and —OSO2-NR20R20, —NR20S(O)2-NR20-alkyl, —NR20S(O)2-NR20-substituted alkyl, —NR20S(O)2-NR20-aryl, —NR20S(O)2-NR20-substituted aryl, —NR20S(O)2-NR20-heteroaryl, —NR20S(O)2-NR20-substituted heteroaryl, —NR20S(O)2-NR20-heterocyclic, —NR20S(O)2-NR20-substituted heterocyclic, wherein each R20 is independently selected from hydrogen or alkyl, and wherein each of the terms is as defined herein. Representative substituted aryl groups include 4-fluorophenyl, 3-methoxyphenyl, 4-t-butylphenyl, 4-trifluoromethylphenyl, 2-trifluoromethoxyphenyl, 3-trifluoromethoxyphenyl, 4-trifluoromethoxyphenyl, 2-chlorophenyl, 3-chlorophenyl, 4-chlorophenyl, 2-chloro-6-fluorophenyl, 2,4-dichlorophenyl, 4-methoxyphenyl, 3-cyanophenyl, 4-cyanophenyl, 4-phenoxyphenyl, 4-methanesulfonylphenyl, biphenyl-4-yl, and the like.

The term "aryloxy" refers to the group aryl-O— that includes, by way of example, phenoxy, naphthoxy and the like.

The term "substituted aryloxy" refers to substituted aryl-O— groups.

The term "aryloxyaryl" refers to the group -aryl-O-aryl.

The term "substituted aryloxyaryl" refers to aryloxyaryl groups substituted with from 1 to 3 substituents on either or both aryl rings as defined above for substituted aryl.

The term "carboxyl" refers to —COOH or salts thereof.

The term "carboxyl ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)β-cycloalkyl, —C(O)O-substituted cycloalkyl, —C(O)O-aryl, —C(O)O-substituted aryl, —C(O)O-heteroaryl, —C(O)O-substituted heteroaryl, —C(O)O-heterocyclic, and —C(O)O-substituted heterocyclic.

The term "cyano" refers to the group —CN.

The term "cycloalkyl" refers to a saturated or an unsaturated but nonaromatic cyclic alkyl groups of from 3 to 10, 3 to 8 or 3 to 6 carbon atoms having single or multiple cyclic rings including, by way of example, adamantyl, cyclopropyl, cyclobutyl, cyclopentyl, cyclooctyl, cyclohexenyl, and the like.

The term "substituted cycloalkyl" refers to a cycloalkyl group, having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl esters, cycloalkyl, substituted cycloalkyl, heteroaryl, substituted heteroaryl, heterocyclic, and substituted heterocyclic.

The term "cycloalkylene" and "substituted cycloalkylene" refer to divalent cycloalkyl and substituted cycloalkyl groups as defined above.

The term "cycloalkoxy" refers to —O-cycloalkyl groups.

The term "substituted cycloalkoxy" refers to —O-substituted cycloalkyl groups.

The term "halo" or "halogen" refers to fluoro, chloro, bromo, and iodo.

The term "hydroxy" or "hydroxyl" refers to the group —OH.

The term "heteroaryl" refers to an aromatic ring of from 1 to 15 carbon atoms, preferably from 1 to 10 carbon atoms, and 1 to 4 heteroatoms within the ring selected from the group consisting of oxygen, nitrogen, and sulfur. Such heteroaryl groups can have a single ring (e.g., pyridinyl, furyl, or thienyl) or multiple condensed rings (e.g., indolizinyl or benzothienyl) provided the point of attachment is through a ring containing the heteroatom and that ring is aromatic. The nitrogen and/or sulfur ring atoms can optionally be oxidized to provide for the N-oxide or the sulfoxide, and sulfone derivatives. Representative heteroaryl groups include pyridinyl, pyrimidinyl, pyrrolyl, pyrazolyl, indolyl, thiophenyl, thienyl, furyl, and the like.

The term "substituted heteroaryl" refers to heteroaryl groups that are substituted with from 1 to 3 substituents selected from the same group of substituents defined for substituted aryl. Representative substituted heteroaryl groups include 5-fluoro-pyridin-3-yl, 1-benzyl-1H-[1,2,3]triazol-4-yl, 5-bromo-furan-2-yl, trifluoromethyl-2H-pyrazol-3-yl, and the like.

The term "heteroaryloxy" refers to the group —O-heteroaryl, and "substituted heteroaryloxy" refers to the group —O-substituted heteroaryl.

The term "heterocyclyl" or "heterocyclic" refers to a saturated or unsaturated (but not aromatic) group having a single ring or multiple condensed rings, from 1 to 10 carbon atoms, and from 1 to 4 hetero atoms selected from the group consisting of nitrogen, sulfur or oxygen within the ring, wherein in fused ring systems, one or more of the rings can be aryl or heteroaryl provided that the point of attachment is at the heterocycle. The nitrogen and/or sulfur ring atoms can optionally be oxidized to provide for the N-oxide or the sulfoxide, and sulfone derivatives.

The term "substituted heterocyclyl" or "substituted heterocyclic" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzolblthiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

The term "nitro" refers to the group —NO2.

The term "oxo" refers to the atom (=O) or to the atom (—O—).

The term "sulfonyl" refers to the group —S(O)2H.

The term "substituted sulfonyl" refers to the group —SO2-alkyl, —SO2-substituted alkyl, —SO2-alkenyl, —SO2-substituted alkenyl, —SO2-alkynyl, —SO2-substituted alkynyl, —SO2-cycloalkyl, —SO2-substituted cycloalkyl, —SO2-cycloalkenyl, —SO2-substituted cycloalkenyl, —SO2-aryl, —SO2-substituted aryl, —SO2-heteroaryl, —SO2-substituted heteroaryl, —SO2-heterocyclic, —SO2-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Representative sulfonyl groups include methyl-SO2-, phenyl-SO2-, 4methylphenyl-SO2-, and the like.

The term "heterocyclyloxy" refers to the group —O-heterocyclic, and "substituted heterocyclyloxy" refers to the group —O-substituted heterocyclic.

The term "thio" refers to the group —SH.

The term "alkylsulfanyl," "alkylthio," or "thioether" refers to the groups —S-alkyl, wherein alkyl is as defined above.

The term "substituted alkylthio," "substituted alkylsulfanyl," or "substituted alkylthio" refers to the group —S-substituted alkyl, wherein substituted alkyl is as defined above.

The term "cycloalkylthio" or "cycloalkylsulfanyl" refers to the groups —S-cycloalkyl wherein cycloalkyl is as defined above.

The term "substituted cycloalkylthio" refers to the group —S-substituted cycloalkyl wherein substituted cycloalkyl is as defined above.

The term "arylthio" or "arylsulfanyl" refers to the group —S-aryl, and "substituted arylthio" refers to the group —S-substituted aryl, wherein aryl and substituted aryl are as defined above.

The term "heteroarylthio" or "heteroarylsulfanyl" refers to the group —S-heteroaryl, and "substituted heteroarylthio" refers to the group —S-substituted heteroaryl, wherein heteroaryl and substituted heteroaryl are as defined above.

The term "heterocyclicthio" or "heterocyclicsulfanyl" refers to the group —S-heterocyclic, and "substituted heterocyclicthio" refers to the group —S-substituted heterocyclic wherein heterocyclic, and substituted heterocyclic are as defined above.

The term "ester" refers to the group —C(O)OR21, wherein R21 is alkyl, substituted alkyl, aryl, or substituted aryl.

In one embodiment, in Formula (I), R1 and R5 are hydroxyl; R2, R3, R4, R7, R9, and R10 are hydrogen; R6 is methyl; and R8 is phenox, and the compound has a structure shown below in formula (II). This molecule is also known as FG-4592 (aka. Roxadustat), which is an isoquinolone having the chemical name, N-[(4-hydroxy-1-methyl-7-phenoxyisoquinolin-3-yl)carbonyl]glycine)].

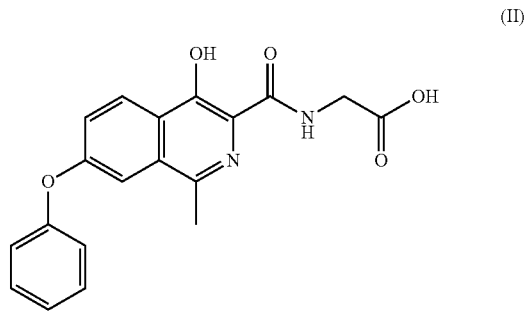 [SMILES: Cc1nc(C(=O)NCC(=O)O)c(O)c2ccc(Oc3ccccc3)cc12]

(II)

FG-4592 (Roxadustat) is in phase 3 clinical trials for the treatment of anemia in chronic kidney disease with no untoward effects reported.

In a specific embodiment, FG-4592 (Roxadustat) is administered at an amount between 0.2 mg/kg and 10 mg/kg. In another embodiment the dosage of FG-4592 (Roxadustat) is 0.2 mg/kg, 0.5 mg/kg, 5 mg/kg, 8 mg/kg, 10 mg/kg, 15 mg/kg or 20 mg/kg.

In another specific embodiment, the HIF stabilizer is dimethyloxalylglycine (DMOG, amino dicarboxylic acid with flanking methyl groups; chemical name N-(2-Methoxy-2-oxaoacetyl)glycine methyl ester). DMOG has the flowing chemical structure:

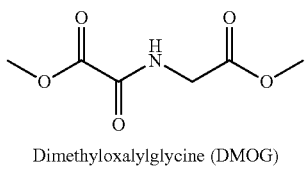

Dimethyloxalylglycine (DMOG)

In a specific embodiment, DMOG is administered at an amount between 50 mg/kg and 200 mg/kg. In another embodiment the dosage of DMOG is 50 mg/kg, 75 mg/kg, 100 mg/kg, 125 mg/kg, 150 mg/kg, 175 mg/kg or 200 mg/kg.

In an embodiment, a HIF stabilizer can be combined with a pharmaceutically acceptable carrier prior to administration. For the purposes of this disclosure, "pharmaceutically acceptable carriers" means any of the standard pharmaceutical carriers. Examples of suitable carriers are well known in the art and may include, but are not limited to, any of the standard pharmaceutical carriers such as a phosphate buffered saline solution and various wetting agents. Other carriers may include additives used in tablets, granules and capsules, and the like. Typically such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well-known conventional methods.

A HIF stabilizer can be admixed with a pharmaceutically acceptable carrier to make a a pharmaceutical preparation in any conventional form including, inter alia, a solid form such as tablets, capsules (e.g. hard or soft gelatin capsules), pills, cachets, powders, granules, and the like; a liquid form such as solutions, suspensions; or in micronized powders, sprays, aerosols and the like.

In some embodiments, the composition of the present disclosure can be administered by different routes of administration such as oral, oronasal, or parenteral route.

"Oral" or "peroral" administration refers to the introduction of a substance into a subject's body through or by way of the mouth and involves swallowing or transport through the oral mucosa (e.g., sublingual or buccal absorption) or both.

"Oronasal" administration refers to the introduction of a substance into a subject's body through or by way of the nose and the mouth, as would occur, for example, by placing one or more droplets in the nose. Oronasal administration involves transport processes associated with oral and intranasal administration.

"Parenteral administration" refers to the introduction of a substance into a subject's body through or by way of a route that does not include the digestive tract. Parenteral administration includes subcutaneous administration, intramuscular administration, transcutaneous administration, intradermal administration, intraperitoneal administration, intraocular administration, and intravenous administration.

In some embodiments, compositions comprising a HIF stabilizer can be administered by aerosol. For example, this can be accomplished by preparing an aqueous aerosol, liposomal preparation or solid particles containing a composition comprising a HIF stabilizer preparation. A nonaqueous (e.g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound.

In another aspect of the present disclosure, a HIF stabilizer is used in a method of preventing CLD in preterm neonates. In a specific embodiment a HIF stabilizer is administered to a preterm at a dose between 0.2 mg/kg and 200 mg/kg, depending on the HIF stabilizer used and the route of administration chosen. In other embodiments, the HIF stabilizer is administered at a dose about 0.2 mg/kg, 0.5 mg/kg, 8 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 150 mg/kg, 175 mg/kg or 200 mg/kg of HIF stabilizer.

In yet another embodiment, a HIF stabilizer is administered to a patient in need thereof every day. In another embodiment a HIF stabilizer is administered intermittently every two days or every three days. In yet another embodiment, a HIF stabilizer is administered during oxygen supplementation sessions, and HIF stabilizer administration is stopped once the neonate is no longer on supplemental oxygen. In a specific embodiment HIF stabilizer are administered once a week. Administration of HIF stabilizer can be continued until the neonate can breathe on its own in room air.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The specific examples listed below are only illustrative and by no means limiting.

EXAMPLES

Materials and Methods

Animals. All experimental procedures involving live animals were conducted in accordance with the guidelines of the NIH Guide for the Care and Use of Laboratory Animals and approved by the Weill Cornell Medicine and Cleveland Clinic institutional animal care and use committee. Wild type C57BL/6 mice were supplied by Harlan and Jackson Laboratory. Wild type CD1 mice were supplied by Charles River. Luc-ODD transgenic mouse expressing HIF-1α oxygen-dependent degradation domain fused to luciferase was purchased from Jackson Laboratory (stock 6206). Conditional liver Hif1a knockout mouse was generated at Jackson Laboratory by crossing Hif1a$^{2lox/2lox}$ mouse (stock 7561) with Albumin-Cre mouse (stock 3574).

Prolyl hydroxylase inhibitors. Dimethyloxalylglycine (DMOG) from Frontier Scientific was directly dissolved in sterile PBS to a stock concentration of 20 mg/mL then filter-sterilized again and stored aliquoted at −80° C. Roxadustat (FG-4592) was supplied by Selleck Chemicals and by AdooQ BioScience; 50 mg/mL stock solution was first prepared in DMSO then further diluted in sterile PBS to 1 mg/mL and stored aliquoted at −80° C. The inhibitors were administered to newborn pups by i.p. injections via a 31-gauge needle at a typical dose of 200 mg/kg (DMOG) or 10 mg/kg (Roxadustat) unless specified otherwise.

Detection of luc-ODD luciferase reporter in vivo and in vitro. Live imaging of luciferase activity was performed using Bruker Xtreme small animal x-ray, fluorescence bioluminescence imaging system. Luc-ODD mouse pups at 12 days of age (P12) were divided into appropriate experimental groups identified by ear notches and treated according to the experimental design, i.e., various length of pharmacological treatment (0, 3, 9, 24 hrs), or route of administration (intraperitoneal vs subcutaneous for 3 hrs). At a designated time following the treatments with PBS or Roxadustat pups received i.p. injection of 50 mg/kg VivoGlo luciferin (Promega) and were anesthetized in the induction chamber by oxygen/isofurane flow. Ten minutes later, pups (in groups of 2 to 4) were placed in an imaging chamber supplied with a heated pad and inhalation cones for oxygen/isofurane mixture. Ventral and dorsal bioluminescent images were collected for 30 sec followed by white light images taken at autoexposure time. Light and luminescent images where then superimposed and quantitatively analyzed using Bruker MI v7 software. Luciferase activity in mouse organs was detected as follows. Luc-ODD mouse pups at P8 were treated with PBS or Roxadustat by a single i.p. injection followed by lethal anesthesia and organ dissection. Tissues were placed in Glo Lysis Buffer (Promega), homogenized with disposable plastic pestles fitted to 1.5 mL microtubes on ice and centrifuged at 20,000×g, 4° C., for 15 min. Protein concentrations of tissue extracts were determined using BCA Protein Assay (Thermo Sci), adjusted to 150 ug (retina), 300 ug (kidney, spleen, lung) or 600 ug (brain, liver) per assay reaction by diluting with Glo Lysis Buffer in a total volume of 100 uL and placed in the wells of white opaque 96-well plate. Diluted extracts were then brought to room temperature, mixed with equal volume (100 uL) of ready-to-use luciferase substrate Bright-Glo Luciferase Assay System (Promega) and luminescence was measured immediately by a luminometer/fluorimeter Victor X2 (PerkinElmer).

Cell culture. Human hepatoma cell line Hep3B (from ATCC) and human Muller cell line MIO-M1 (provided by Dr. G. Astrid Limb, Moorfields Eye Hospital, London, UK) were grown in DMEM, 10% FBS, penicillin, streptomycin. Cell were plated into 6-well clusters for protein analysis or 60 mm Petri dishes for RNA isolation, allowed to reach confluent state and then treated with 10 ug/mL Roxadustat overnight in the presence of serum. Cell culture samples were harvested by washing cell monolayers with PBS, scarping cells in ice-cold RIPA buffer (Sigma-Aldrich) containing protease (Complete) and phosphatase (PhosSTOP) inhibitors (Roche) for protein extraction or in RLT buffer (Qiagen) containing 1% 2-mercaptoethanol for RNA isolation (below).

Western blot analysis. Following a pharmacological treatment specified in the figure legends (drug, duration, route and dosage), mouse pups were sacrificed by lethal injection of ketamine/xylazine, organs (liver, kidney, brain) were quickly dissected and immediately placed in RIPA+inhibitors, while enucleated eyes were first placed in cold PBS, immediately dissected to obtain retina, which was then moved to RIPA+inhibitors. Tissues were homogenized on ice by a pestle in a 1.5 mL microtube, protein extracts were cleared by 20,000×g centrifugation, at 4° C., for 15 min, and their protein concentrations were measured by BCA Protein Assay (Thermo Sci). Equal amounts of total protein were loaded, resolved by SDS-PAGE using precast Novex gradient 4%-20% Tris-Glycine gels (Life Technologies) and electro-transferred to PVDF membranes. Such membranes were then blocked in 5% non-fat milk dissolved in 0.1% Tween 20 in Tris buffered saline and incubated with anti-mouse HIF-1α rabbit polyclonal (Cayman Chemical, cat #10006421) or anti-human mouse monoclonal HIF-1α (BD Transduction Labs, cat #610958) antibody. After overnight incubation at 4° C. with primary antibodies, HRP-conjugated secondary antibodies (Jackson ImmunoResearch Labs) followed by Western Lightning (PerkinElmer) substrate reagent and x-ray film (Kodak MR) were used to reveal chemiluminescent signal.

Reverse transcription and quantitative PCR. Mouse tissue procurement was described above. Tissue from liver, kidney, brain and retina were placed into 1 mL of RNAlater reagent (Qiagen) and stored at −80° C. Total RNA was extracted using RNeasy kit (Qiagen) and measured using NanoDrop and standard spectrophotometric parameters. One μg of total RNA from each sample was retrotranscripted to cDNA using QuantiTect Reverse Transcription Kit (Qiagen). One μl of cDNA samples was used as template for amplification reactions carried out with the QuantiTect SYBR Green PCR kit (Qiagen) following the manufacturer's instructions. PCR amplifications were performed in a 7900HT Fast Real-Time PCR system (Applied Biosystems) and quantitative PCR data analysis was performed with RQ Manager software (Applied Biosystems).

Mouse Studies

For this study we utilized a well-defined murine model of CLD using neonatal mice chronically exposed to hyperoxia for 2 weeks followed by normoxia for an additional 3. Timed pregnant mice were monitored hourly. Within hours of birth litters were pooled before being randomly redistributed to the newly delivered mothers. Experiments were begun on newborns at postnatal day 0. Half of the newborn pups were placed in a chamber designed to deliver variable oxygen concentrations (Biospherix Ltd) and set to 80% $O_2$ (HO) and the other half remained in room air (RA) as age-matched controls. Mothers were rotated every 12 hours to prevent death from acute $O_2$ toxicity. Neonatal CD1 mice also referred to as wild-type mice (Charles River), MCD mice (WBB6F1-$^{W/Wv}$) and their mast cell competent litter mates WBB6F1-$^{+/+}$ (congenic controls (CC)) (Jackson Laboratories) were exposed to either HO or RA for 2 weeks and then kept in room air ($F_iO_2$ of 0.21) an additional 3 weeks for the 5-week time point. Some CD1 mice (HO and RA) were also maintained 18 weeks in room air for the 20-week time point. Survival and weight were monitored daily. All mice (CD1, MCD, and CC) used in this study were healthy at birth and survived until sacrificed. Unless specifically noted as CC or MCD, mouse experiments were performed with CD1 mice.

Approvals

Animal studies were conducted under protocols approved by the Institutional Animal Care and Use Committee of Weill Cornell Medicine.

Blood collection and ELISA of serum proteins. Mouse pups at the age of P8 were treated by i.p. injection of PBS or 10 mg/kg Roxadustat for various periods of time. Blood was obtained by cardiac puncture as follows. Mouse pups were anesthetized by i.p. 100 mg/kg Ketamine:10 mg/kg Xylazine, their abdominal cavity was opened and the beating heart was accessed through a cut in the diaphragm. Blood was drawn into 1 cc insulin syringe with 27-gauge needle inserted into the left ventricle (heart apex). The animal was then sacrificed by exsanguination. To obtain serum blood was allowed to coagulated for 1-2 hr at room temperature followed by the clot contraction overnight at 4° C. and removal of any residual uncoagulated cellular elements by low speed centrifugation at 2,000 rpm for 5 min. To detect EPO or VEGF serum was diluted 1:10 and to detect PAI-1 serum was diluted 1:100 with sample diluent provided by the manufacturer of colorimetric ELISA kits for mouse EPO, VEGF or PAI-1 (R&D Systems). Spectrophotemetric detection and quantification of serum proteins were performed according to the manufacturer's instructions.

Oxygen-induced lung injury and lung airspace analysis. A well-defined murine model of CLD, a.k.a. bronchopulmonary dysplasia, using neonatal mice chronically exposed to hyperoxia followed by normoxia was used for our studies. Timed pregnant CD1 mice (Charles River) were monitored hourly. Within hours of birth litters were pooled before being randomly redistributed to the newly delivered mothers. Half of the newborn pups were immediately placed in a chamber designed to deliver variable oxygen concentrations (Biospherix) and set to 80%, 45% or 30% $O_2$ (hyperoxia) and the other half remained in room air. Mothers were rotated every 12 hrs to prevent death from acute $O_2$ toxicity. Newborn pups were exposed to either hyperoxia or room air for 2 weeks. During the hyperoxia exposure, mice were given a subcutaneous injection of 10 mg/kg body weight of Roxadustat every other day for a total of 5-7 doses, starting on the first day of life. Some animals were then kept in room air for an additional 3 weeks or 18 weeks before analysis. Lungs from mice were fixed at a constant inflation pressure of 25 cm $H_2O$ in 10% neutral buffered formalin followed by paraffin embedding. Sections (7 µm) were cut and slides of paraffinized tissue sections were deparaffinized, rehydrated, and washed in distilled water. Sections were stained with hematoxylin and eosin to visualize the structure of the lung.

The direct method was used for the accurate estimation of the mean linear intercept length (Lm) (chord length) to assess the mean free distance in the alveoli. This method uses a set of random intercepts and calculates Lm from their frequency distribution and provides results on alveolar size distribution and alveolar surface area. Tissue sections were viewed under transmitted light with a 10× objective and an inverted epifluorescence microscope (Nikon Eclipse TE 2000-U) interfaced to a SPOT Insight 2 megapixel color camera (Diagnostic Instruments) and processed with Metamorph software (version 6.2, Universal Imaging Corp). Entire tissue sections were imaged by capturing adjacent, non-overlapping fields. On average 30-50 non-overlapping 1 mm² fields were analyzed for each lung section. Mean chord length of each alveolus (µm) was measured with the areas of approximately 4,000 individual alveoli/mouse measured in sections from room air mice and about 2,000 individual alveoli/mouse were analyzed in lung sections from hyperoxic mice.

Lung Mechanics

Pulmonary function tests (PFTs) were performed in 5- (CD1, MCD and CC) and 20-week old mice (CD1) post-neonatal HO or RA. Briefly, mice were anaesthetized with pentobarbital (100 mg/kg, intraperitoneal; American Pharmaceutical Partners), tracheostomized and mechanically ventilated at a rate of 150 breaths/min, a tidal volume of 10 ml/kg and positive end-expiratory pressure of 2-3 cm $H_2O$ using a computer-controlled animal ventilator (Sireq). The following perturbations were used to assess baseline respiratory mechanics and analyzed using Flexivent software (Sireq). Static lung compliance (Cst) was determined using the Salazar-Knowles equation applied to the plateau pressure measurements obtained between total lung capacity and functional residual capacity. Broadband forced oscillations were applied to determine tissue resistance (R) and Newtonian (airway) resistance (Rn) using a constant phase model. Mice used for measuring pulmonary function were not used for histological analyses.

Tissue Histochemical Techniques

Lungs from mice (CD1, MCD and CC), not undergoing pulmonary function testing, were fixed at a constant inflation pressure of 25 cm $H_2O$ in 10% neutral buffered formalin followed by paraffin embedding. Slides with 7 µm sections were deparaffinized, rehydrated, and washed in distilled water. Some sections were stained with hematoxylin and eosin (H&E) to visualize the structure of the lung. Other sections were stained with an antibody (CC10) (Santa Cruz Biotechnology) (1:50 dilution) to detect club cells, a cell type specific to the airways. Analysis on the alveolar space deliberately avoided airways and blood vessels. For each animal, 5 lung sections were analyzed and quantified as cells per mm² of lung tissue.

Mast cells were detected in fixed tissue using either the glycoprotein avidin, conjugated to the enzyme horseradish peroxidase (HRP) (Vector Laboratories) or toluidine blue, the classic metachromatic stain for mast cells. Conjugated avidin is a well-defined histochemical method for identifying rodent and human mast cells, which express chondroitin sulfate E proteoglycans and heparin proteoglycans, respectively, in the secretory granules, binding specifically to the proteoglycan granules. Non-specific staining of biotin or biotin-like molecules previously reported were observed. Deparaffinized sections were exposed to avidin-HRP 1:500. NovaRED (Vector Laboratories) was used as the chromogen substrate, according to the manufacturer's instructions.

Additional sections were immunoscreened for neutrophils, macrophages, B cells, and T cells. Following antigen retrieval with 10 mM sodium citrate buffer at 98° C. for 20 minutes, rat anti-Ly-6G/-6C (1:50), rabbit anti-B220 (1:100), rabbit anti-CD3 (1:100), rabbit anti-Mac-2 (1:50) primary antibodies (abcam) were added followed by incubation with the appropriate HRP-conjugated secondary antibody (Jackson Laboratories).

Gomori's Trichrome staining was performed using a dilution of Weigert's hematoxylin at 1:10 as previously described. Sections were stained using components from the trichrome kit and according to the manufacturer's protocol. After dehydrating and clearing in xylene, the sections were mounted with coverslips in Vectamount (Vector Laboratories, CA).

For all histological analyses tissue sections were viewed under transmitted light with a 10× objective and an inverted epifluorescence microscope (Nikon Eclipse TE 2000-U) interfaced to a SPOT Insight 2 megapixel color camera (Diagnostic Instruments) and processed with Metamorph software (version 6.2; Universal Imaging Corp.). All histological analyses and cell number quantifications were performed by two investigators in a blinded fashion.

Lung Airspace Analysis

The direct method was used for the accurate estimation of the mean linear intercept length ($L_m$) (chord length) to assess the mean free distance in the alveoli. Entire tissue sections were imaged by capturing adjacent, non-overlapping, fields. On average 30-50 non-overlapping 1 $mm^2$ fields were analyzed for each lung section and mean chord length of each alveolus (μm) was measured.

Western Blotting

Aliquots of purified TA and HMC-1 exosomes were homogenized and the protein amounts determined by Lowry assay. Primary antibodies used were: mouse monoclonal TSG 101 (Santa Cruz sc-7964) at 1:500 dilution, mouse monoclonal Alix (Cell Signaling, 2171) at 1:1000 dilution, rabbit polyclonal CD63 (Santa Cruz, sc-15363) at 1:500 dilution, rabbit polyclonal chymase at a 1:2500 dilution (Abcam, 186417), mouse monoclonal mast cell tryptase (Abcam, ab2378) at 1:3000 dilution, rabbit polyclonal elastase (Abcam, ab68672) at 1:1000 dilution, mouse monoclonal mast cell CPA3 (Abcam, ab72575) at 1:500 dilution, and mouse monoclonal GAPDH (Cell Signaling, 14C10) and β-actin (Cell Signaling, 3700) at 1:100,000 dilution. GAPDH and β-actin were used as loading controls.

Quantitative PCR

Lungs from 2- and 5-week old mice (CD1) were quickly excised, washed in cold PBS, cut in half and then snap frozen in liquid nitrogen and stored at −80° C. To isolate the RNA, 15 mg of lung tissue was homogenized, then RNeasy (Qiagen, Valencia, Calif.) protocol was followed. RNA was quantified using a Nanodrop spectrophotometer (Thermo Scientific, Waltham, Mass.). 0.76 ug of RNA were reverse transcribed using the High Capacity RNA-cDNA kit (Applied Biosystems, Foster City, Calif.). QPCR was performed at 1/10 dilution using fast SYBR green master mix (Applied Biosystems, Foster City, Calif.) for mouse CPA3, TPSAB1, and TPSAB2 genes. GAPDH was used as the housekeeping gene and expression was constant. QPCR was done on a Step One real time PCR system (Applied Biosystems, Foster City, Calif.).

The primers were as follows:

```
                                            (SEQ ID NO: 1)
CPA3
forward     AATTGCTCCTGTCCACTTTGAC;

(SEQ ID NO: 2)
reverse     TCACTAACTCGGAAATCCACAGT, (SEQ ID NO: 3)
TPSAB1
forward     GCCAATGACACCTACTGGATG;

(SEQ ID NO: 4)
reverse     GAGCTGTACTCTGACCTTGTTG, (SEQ ID NO: 5)
TPSAB2
forward     CTGGCTAGTCTGGTGTACTCG;

(SEQ ID NO: 6)
reverse     CTGGCTAGTCTGGTGTACTCG, (SEQ ID NO: 7)
GAPDH
forward     AACAGCTCCCACTCTTC;

(SEQ ID NO: 8)
reverse     CCTGTTGCTGTAGCCGTATT.
```

All RNA samples had a 260/280 ratio of 1.8 or higher—indicating RNA purity of samples.

TA exosomes—Exosome pellets were dissolved in RNeasy lysis buffer (Qiagen, Valencia, Calif.). RNA was isolated and quantified as above. 45 ng of RNA were reverse transcribed using the High Capacity RNA-cDNA kit (Applied Biosystems, Foster City, Calif.). QPCR was performed at 1/4 dilution using fast SYBR green master mix (Applied Biosystems, Foster City, Calif.) for human CPA3, TPSAB1, TPSAB2, and GAPDH genes able to detect as low as 1 copy of target DNA.

Human primers were as follows:

```
                                            (SEQ ID NO: 9)
CPA3
forward     GGGTTTGATTGCTACCACTCTT;

(SEQ ID NO: 10)
reverse     GCCAAGTCCTTTATGATGTCTGC, (SEQ ID NO: 11)
TPSAB1
forward     GTGACGCAAAATACCACCTTGGC;

(SEQ ID NO: 12)
reverse     CATTCACCTTGCACACCAGGG, (SEQ ID NO: 13)
TPSAB2
forward     CCGCGACCGATACTGGATG;

(SEQ ID NO: 14)
reverse     GATCTGGGCGGTGTAGAACT, (SEQ ID NO: 15)
GAPDH
forward     CAACAGCACAGGAGAG;

(SEQ ID NO: 16)
reverse     CTACATGGCAACTGTGAGGAG.
```

Statistical analysis. Aside from biostatistical processing of RNA-seq data, regular statistical analyses of all other data (qPCR, image density or pixel number quantification) were performed by comparing means using Student's t-test. The two-tailed probability associated with rejecting the null hypothesis of no difference between observed groups was calculated, using an alpha level of 0.05. Error bars in all figures represent SD.

To ensure a robust and unbiased approach equal numbers of male and female mice were used. Male and female mouse pups from different mothers were pooled together and randomly allocated to experimental groups after birth in unbiased way. The treatment assignment was blinded to investigators who participate in the endpoint analyses. The outcome parameters include: 1. Chord lengths, 2. Compliance, 3. Mast cell numbers, 4. Inflammatory score, 5. Remodeling score via Masson's trichrome analysis as previously described. Immune and inflammatory cells were counted in ten high-power fields (400×) in each slide and averaged together. Number of mice (N) for the groups will range from 8 (for biochemical and histological analyses) to 10 for the pulmonary function testing and airway responsiveness. All histological analyses and cell number quantifications were performed by two investigators in a blinded fashion. Statistical comparisons were conducted by one-way ANOVA or unpaired Student's t-test using GraphPad Prism 5.0 software. A 95% confidence level was considered statistically significant.

Example 1: Hypoxia Inducible Factor Prolyl Hydroxylase Inhibition (HIP PHi)

Detection of organ specific HIF PHi using the luciferase-oxygen dependent degradation domain mouse (luc-ODD) correlates to organ specific HIF-1α stabilization (FIG. 1). The luc-ODD mouse has a transgene comprised of luciferase fused to the ODD, and therefore serves as a reporter gene in vivo of where hydroxylation of the ODD is inhibited, observed as luminescence in tissue lysates and whole animal imaging. Ventral and dorsal views (FIG. 3A) of the luc-ODD mouse show highest luminescence in the liver and kidney respectively, which are targeted by either intraperitoneal (i.p.) or subcutaneous injections of Roxadustat. Quantitation supports the specificity of this effect in tissue lysates and shows 6-fold luciferase activity over baseline in liver (FIGS. 3B and 3C). A time course of HIF stabilization in kidney and liver revealed that a single i.p. injection of Roxadustat provides HIF PHD inhibition for at least 24 hours with a half-life of 2-3 days (FIG. 3D). Organ-specific elevation of HIF-1α protein was detected by Western blotting, with a 5-10 fold increase in liver and kidney and weaker but definite two-fold increase in spleen, lung, brain, and retina (FIGS. 3E and 3F). The kinetics of HIF stabilization by Roxadustat (FIG. 3G) is similar to luminescence activity in the luc-ODD mouse showing maximal increases in serum erythropoietin (EPO) at 6 hours after i.p. injection (FIG. 3I). This correlates with hepatic expression of Epo mRNA (FIG. 3H), as well as 8-fold increase in serum EPO protein concentration in response to Roxadustat (FIG. 3I). Dose response of Roxadustat using serum EPO as a marker of HIF-1 activity demonstrates maximal effect in the mouse of 10 mg/kg bodyweight, within an order of magnitude to the dose used in human adults to increase red blood cell density (FIG. 3J). These effects of Roxadustat on HIF-1α stabilization and expression of EPO, both mRNA and protein, can be recapitulated in cultured hepatoma cells Hep3B (FIGS. 3K and 3L).

Figure 2:
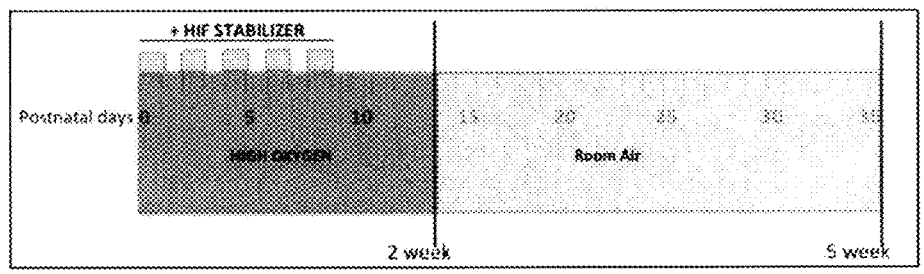
FIG. 2. Diagram of intermittent drug administration according to some embodiments of this invention.
Figures 4A, 4B, 4C, 4D:
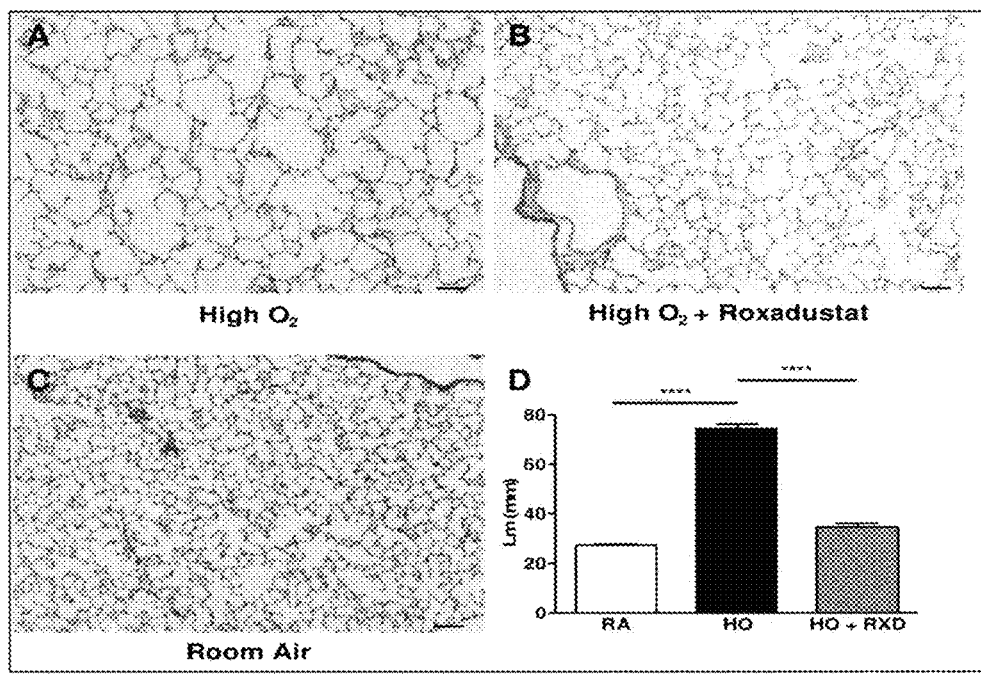
FIGS. 4A-4D. Intermittent treatment with a HIF stabilizer during severe (80%) neonatal hyperoxia normalizes alveolar enlargement. The data shows that lung structure and alveolar size are normalized with HIF stabilization, during exposure to high oxygen at birth. Comparisons of the mice exposed to high oxygen at birth (HO-80%) are to age matched room air controls (RA). Data are from the 5-week time point. Lung histology after hematoxylin and eosin staining demonstrates the destructive alveolar enlargement by hyperoxia (A) that is reduced by subcutaneous Roxadustat (RXD) (B) to the size and structure comparable to age-matched controls in room air (C). Quantification of alveolar size using mean linear intercept (Lm) demonstrates statistically significant normalization in alveolar size by roxadustat (RXD) treatment during hyperoxia in the wild type CD1 mouse pups, ****p=1×10$^{-4}$ (D).

Example 2: HIF Prolyl Hydroxylase Inhibitor Roxadustat Prevents Oxygen Induced Lung Damage The advantage of systemic HIF stabilization was explored by investigating whether Roxadustat (RDX) was also able to protect lung tissue from hyperoxia. Using a well-defined mouse model of oxygen-induced neonatal lung disease followed by normoxia and an intermittent dosing regimen (FIG. 2), pups were given intermittent subcutaneous doses of RXD (10 mg/kg) only during the initial oxygen supplementation phase [High oxygen (HO) (80%) first 2 weeks of life followed by 3 weeks room air (RA)]. Lung histology after hematoxylin and eosin staining demonstrated the destructive alveolar enlargement induced by hyperoxia (FIG. 4A) that was reduced in the lungs of animal treated with Roxadustat to a size and structure comparable to age-matched controls the were not exposed to hyperoxia (FIGS. 4B-C). Assessment of alveolar size by quantification of the chord lengths (Lm) to assess the mean free distance in the alveoli demonstrated normalization in alveolar size by Roxadustat treatment during hyperoxia in the wild-type CD1 mouse pups ($P<0.0001$) (FIG. 4D).

Figures 5A, 5B:
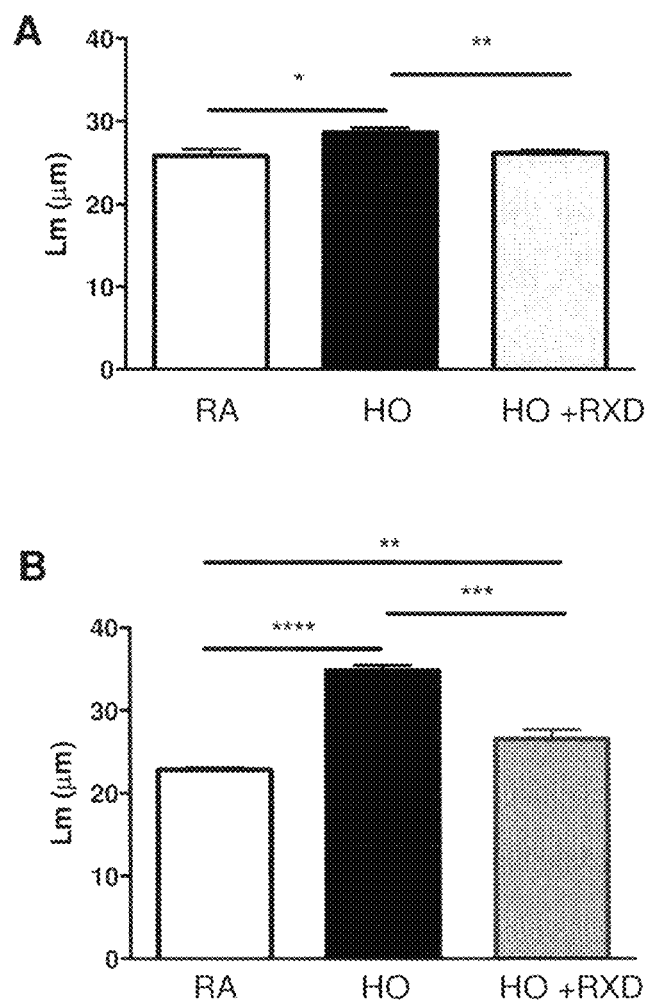
FIG. 5A-5B. HIF Stabilization Protects the Lung Against Moderate (45%) Neonatal High Oxygen. (A) Data from 2-week time point. (B) Data from 5-week time point. Quantification of alveolar size using mean linear intercept (Lm) demonstrates statistically significant normalization in alveolar size by Roxadustat (RXD) treatment during hyperoxia in the wild type CD1 mouse pups. **P<0.0001, *P<0.001, **P<0.01, *P<0.05.
Figure 15:
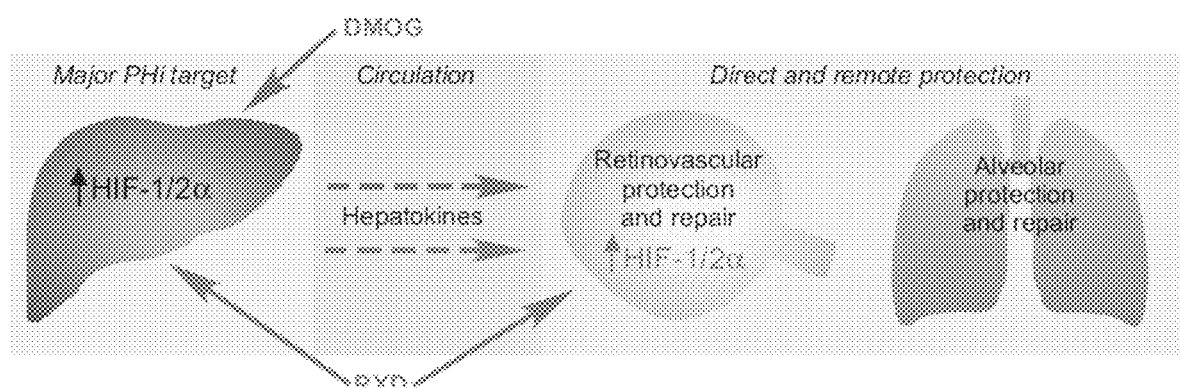
FIG. 15. Schematic representation of the two pathways for retinovascular protection against oxygen-induced retinopathy and bronchopulmonary dysplasia, targeting extraretinal HIF-1 in the liver in the case of DMOG, or both hepatic and retinal HIF-1 pathways in the case of Roxadustat (RXD).

It was also observed that RXD was protective against moderate (about 45%) levels of oxygen at 2 and 5-week time points (FIGS. 5A and 5B). These observations provide basic examples of the power of systemic HIF stabilization because it may address oxygen toxicity to multiple organs (FIG. 15).

Figures 6A, 6B:
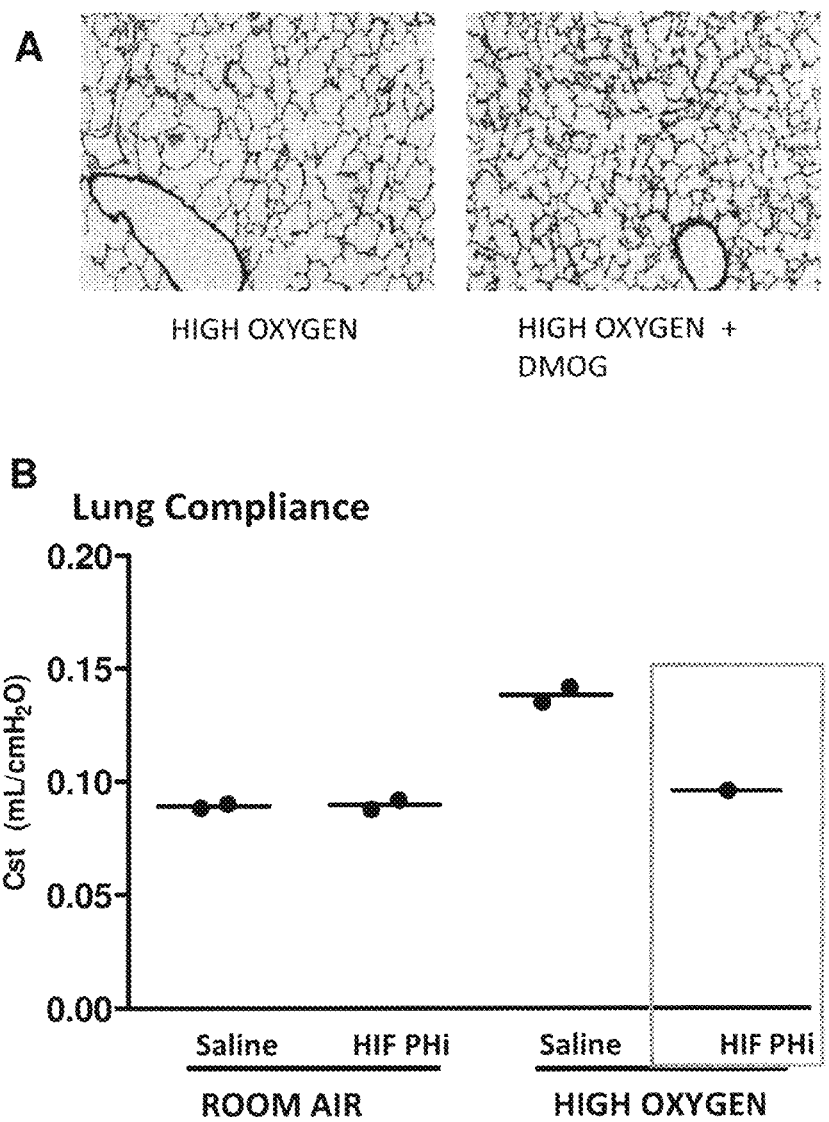
FIGS. 6A-6B. Intermittent treatment with the HIF stabilizer DMOG during severe (80%) neonatal hyperoxia normalizes alveolar enlargement and maintains normal lung compliance. The data shows that lung structure and alveolar size are normalized upon treatment with the HIF stabilizer DMOG, during exposure to high oxygen at birth. (A) Lung histology after hematoxylin and eosin staining of neonatal lungs under high oxygen (left panel), and high oxygen treated with DMOG (right panel). (B) Pulmonary function test of lung compliance.

Example 3: HIF Prolyl Hydroxylase Inhibitor DMOG Prevents Oxygen Induced Lung Damage HIF prolyl hydroxylase inhibition was achieved using a 2-oxoglutarate analogue called dimethyloxalylglycine (DMOG). DMOG was administered to newborn pups by i.p. intermittent injections via a 31-gauge needle at a typical dose of 200 mg/kg (DMOG) (1.14 mmol/kg) only during oxygen supplementation phase. Lung histology after hematoxylin and eosin staining demonstrated the destructive alveolar enlargement induced by hyperoxia (FIG. 6A) that was reduced in the lungs of animal treated with roxadustat to a size and structure comparable to age-matched controls the were not exposed to hyperoxia (FIG. 6A-6B).

Figure 7:
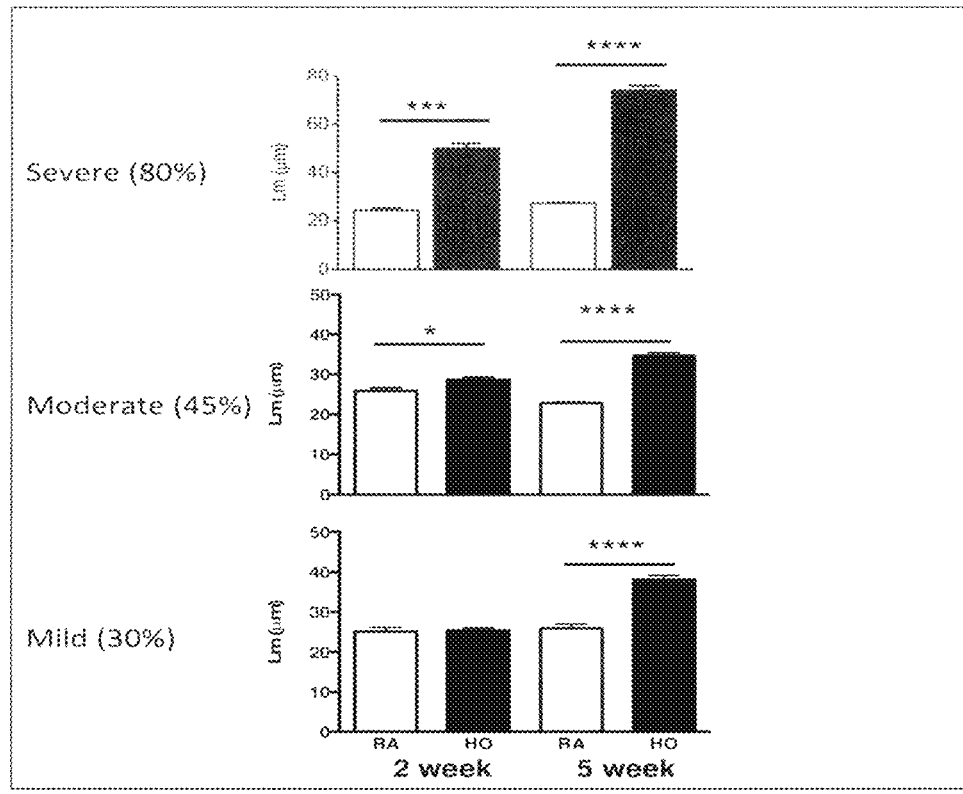
FIG. 7. Alveolar chord length increases with greater oxygen supplementation and continues to increase during recovery in room air (5 week time point). Alveolar chord length Lm (mm) measurements in fixed lung sections from 2- and 5-wk RA and HO (80%) mice. Data are expressed as means±SE. 2-wk: *P<0.001, HO vs. RA, n=4 mice/group; 5-wk: **P<0.0001, HO vs. RA, n=4 mice/group.
Figure 8:
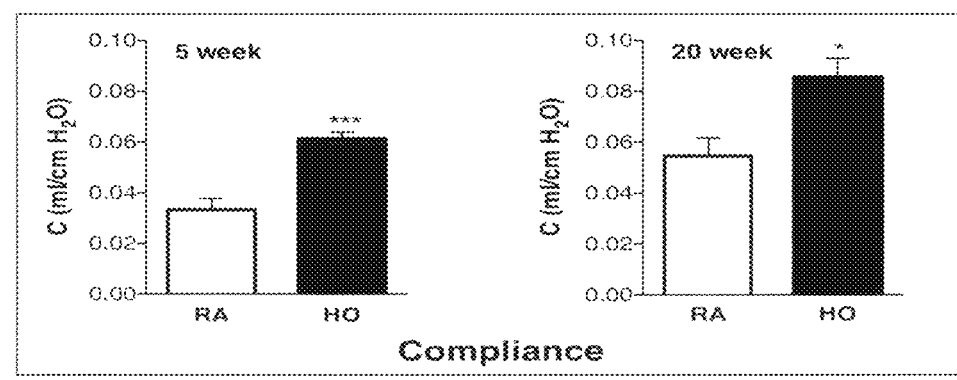
FIG. 8. Analysis of static lung compliance in 5-week and 20-week RA and HO mice. Data are expressed as means±SE. 5-week: ***P<0.001, HO vs. RA, by unpaired Student's t-test, n=6 mice/group. 20-week: Data are expressed as means±SE. *P<0.05, HO vs. RA, n=6 mice/group.

Example 4: Moderate and Mild Neonatal Oxygenation Causes Sustained Lung Damage Given the current management to keep oxygen supplementation to a minimum in premature infants, experiments were performed in neonatal mice for the first 2-weeks of life: 80% (high, severe), 45% (moderate) and 30% (mild). The data suggest that exposures to these lower oxygen concentrations induce a similar enlarged airspace phenotype that is observed following high (80%) oxygen levels (FIG. 7). Also, the damage incurred with HO at the 2-week time point persisted as seen at the 5-week time point suggesting that the damage incurred with hyperoxia is irreversible. Persistent functional damage, as measured by static lung compliance and increased chord lengths, was observed up to 5 months following neonatal exposure to 80% oxygen (FIG. 8). Any intervention that can prevent hyperoxia-induced damage in the neonate will have profound implications on lung health later in life.

Figures 9A, 9B, 9C, 9D, 9E:
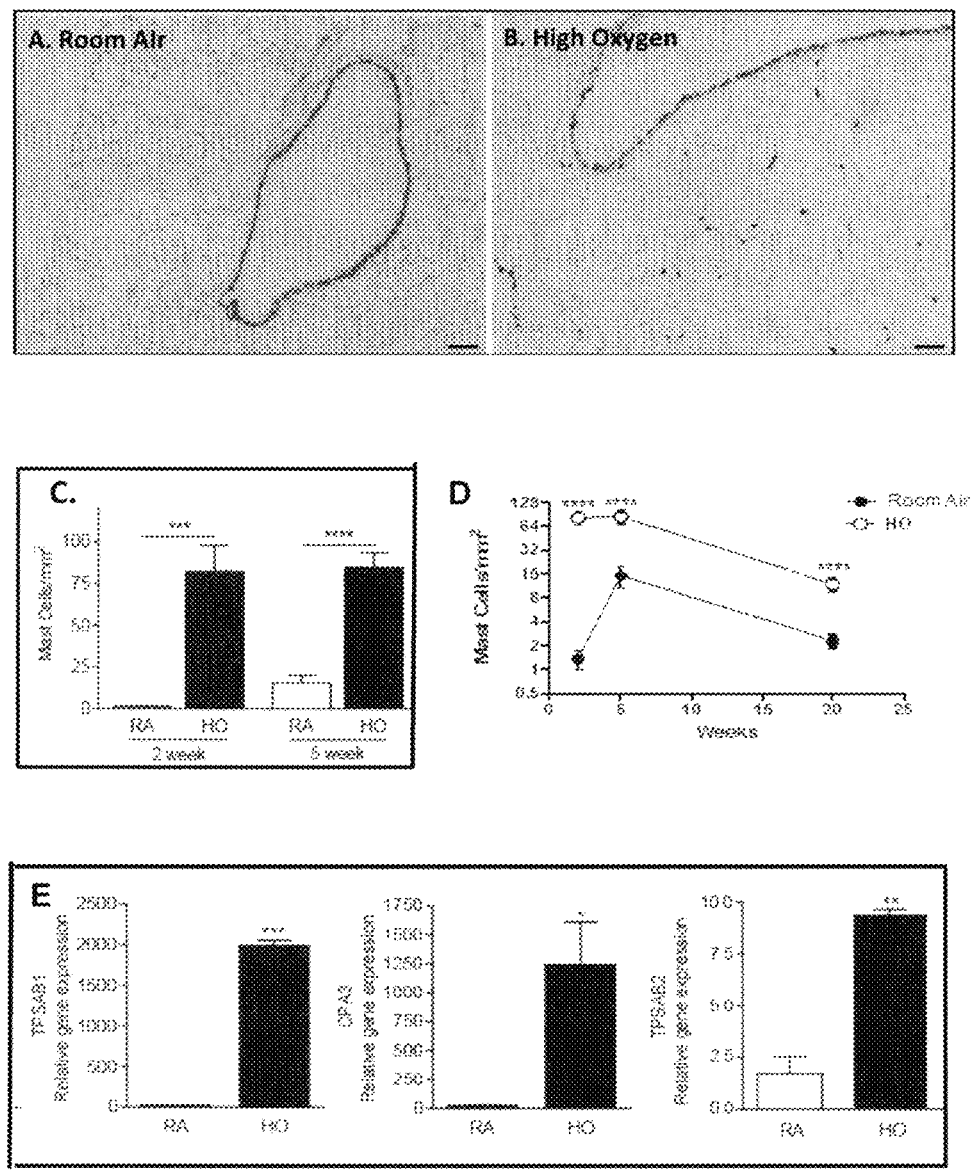
FIGS. 9A-9E. Effect of neonatal hyperoxia on lung mast cells and their transcripts and lung structure and function. Top: Representative photomicrographs of lungs from 2-week old mice kept in room air (A) or exposed to high oxygen (B) the first 2 weeks of life. Mast cells (brown) in the walls of the alveoli are only seen in the high oxygen neonatal lung. Observe the enlarged alveoli in the high oxygen lung compared to the room air lung. Airway club cells are stained blue. Scale bar=50 mm. Room air=RA, high oxygen=HO. (C) Number of mast cells in lung, showing that hyperoxia (80%) increases the mast cell number at the 2- and 5-week time points. N=3 mice/group. **P<0.0001 and *P<0.001. (D) Number of mast cells in lung, showing that hyperoxia increases the mast cell number at every time point compared to room air controls (2-, 5-, and 20-week time points). (E) The mast cell transcripts CPA3, TPSAB1, TPSAB2 are elevated in lung homogenates from HO mice compared to RA controls, 5-week time point. N=3 mice/group. *P<0.001, P<0.01, *P<0.05

Example 5: Effect of Neonatal Hyperoxia on Lung Mast Cells and their Transcripts and Lung Structure and Function The inventors evaluated the effect of neonatal hyperoxia (HO) on the lung mast cell population. A preponderance of mast cells (stained brown) in the alveolar space, an anatomical compartment not typically associated with mast cells, was observed in HO mice (FIG. 9B, 9C, 9D). The number of avidin-positive mast cells present in the HO and RA lungs was quantified. Mast cell infiltration into lung was not seen in RA mice (FIG. 9A, 9C). HO significantly increased the number of mast cells in the lung compared to RA mice immediately following exposure to HO (2-week time point) (P<0.001), and after an additional 3 weeks of breathing room air (5-week time point) (P<0.0001) (FIG. 9B). This finding was verified with toluidine blue staining of HO and RA lung sections from the 2-week time point (HO 85.1±8.5 MCs/mm$^2$ versus RA 4.0±2.8 MCs/mm$^2$; P<0.001).

To determine whether mast cell genes were upregulated in lung tissue we analyzed lung homogenates from the 2- and 5-week time points for mRNA expression of the mast-cell-specific markers TPSAB1, CPA3 and TPSAB2. Expression of all three mast cell genes were increased in the lungs from HO compared to RA mice at both time points. The data from the 5-week time point is shown for TPSAB1 (FIG. 9E, left graph; P<0.001), CPA3 (FIG. 9E, middle graph; P<0.05) and TPSAB2 (FIG. 9E, right graph; P<0.01). These results are consistent with the observed increases in the lung mast cell population.

The area of the airspaces in lungs quantified by measuring chord length ($L_m$) was greater in lungs from HO compared to RA mice both at 2 weeks (P<0.001) and 5 weeks (P<0.0001) (FIG. 9C).

Figure 10A:
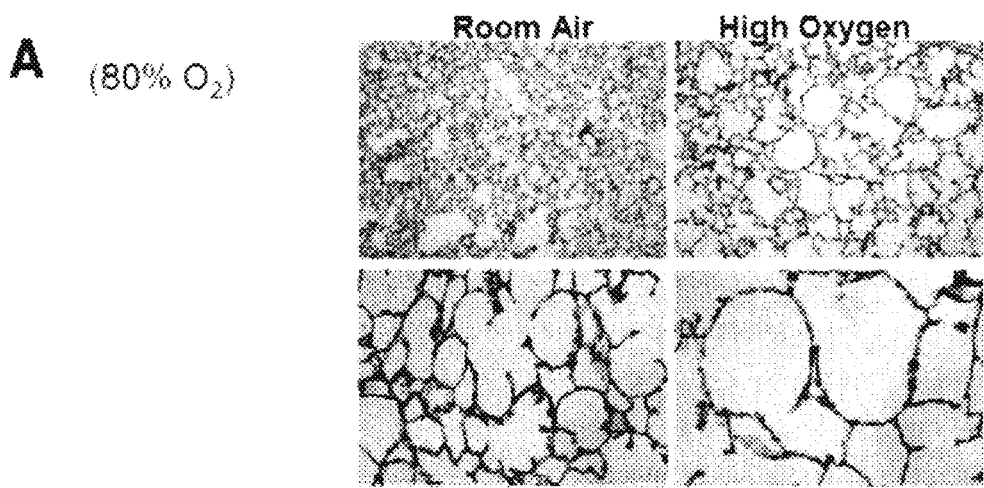
FIGS. 10A-10C. Neonatal hyperoxia leads to enlarged airspaces and impaired lung function. (A) Representative photomicrographs of lungs of mice kept in room air or exposed to high (80%) oxygen. (B) Mean chord length of each alveolus (μm) was measured with the areas of approximately 4,000 individual alveoli/mouse measured in sections from room air mice and about 2,000 individual alveoli/mouse were analyzed in lung sections from hyperoxic mice. **P<0.0001 and *P<0.001. (C) Static lung compliance (Cst) was determined in 5-week old mice (left graph) and 20-week old mice (right graph) using the Salazar-Knowles equation applied to the plateau pressure measurements obtained between total lung capacity and functional residual capacity. Broadband forced oscillations were applied to determine tissue resistance (R) and Newtonian (airway) resistance (Rn) using a constant phase model.
Figure 10B:
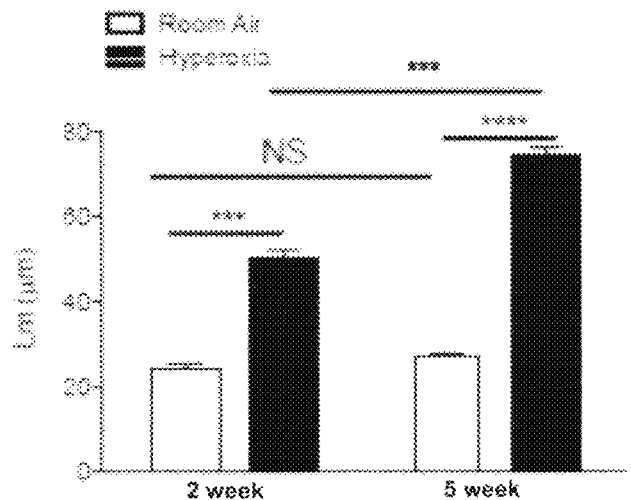
Figure 10C:
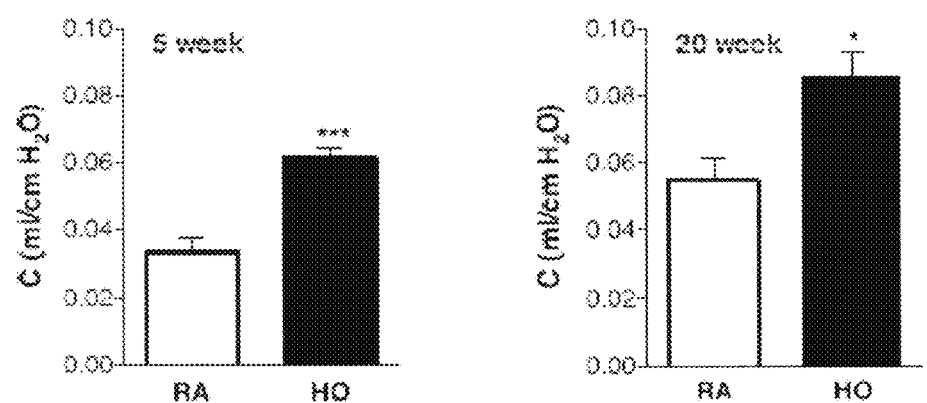

Consistent with the enlarged airspace, static lung compliance was increased in HO mice compared to RA at the 5- (FIG. 10C, left graph; P<0.001) and 20-week (FIG. 10C, right graph; P<0.05) time points indicating a sustained change in lung function. We did not detect a change in lung tissue resistance (R) or airway resistance (Rn) either at the 5- or 20-week time points. Fixed lung sections from HO and RA mice from the 5- and 20-week time points were screened for fibrosis. Fibrosis was not detectable in any samples. Similar results describing an attenuated phenotype of CLD with no changes in airway resistance have been reported by others using similar mouse models (Velten M. et al., *J Appl Physiol*, (2010) 108: 1347-1356; Wang H. et al., *American Journal of Physiology Lung Cellular and Molecular Physiology* 307: L295-301, 2014).

Collectively these data show that neonatal hyperoxia leads to an increase in lung mast cells and a persistent and impaired alveolar phenotype, the latter leading to increases in lung compliance.

Example 6: Effect of Mast-Cell-Deficiency on Lung Function and Structure in Neonatal Hyperoxia.

Mast-cell-deficiency protects against neonatal hyperoxia-induced enlarged airspaces and increased lung compliance. To directly determine the role of mast cells in the lung pathology associated with neonatal hyperoxia, experiments were performed in 5-week old MCD and CC mice. HO did not lead to alveolar enlargement as in the CC mouse lungs. In RA conditions, the alveolar airspace, as determined by chord length, was not significantly different between the 5-week MCD and CC mice. Exposure to HO increased $L_m$ in the CC group (P<0.0001) but not in the MCD mice. In accordance, lung compliance only increased in the CC group exposed to hyperoxia (P<0.05) and not in the MCD mice exposed to hyperxia. These results describe a connection between mast cells and the structural and functional changes in the lung associated with neonatal hyperoxia.

Example 7: Mild and Moderate Neonatal Hyperoxia Increases Lung Mast Cells

Figure 11:
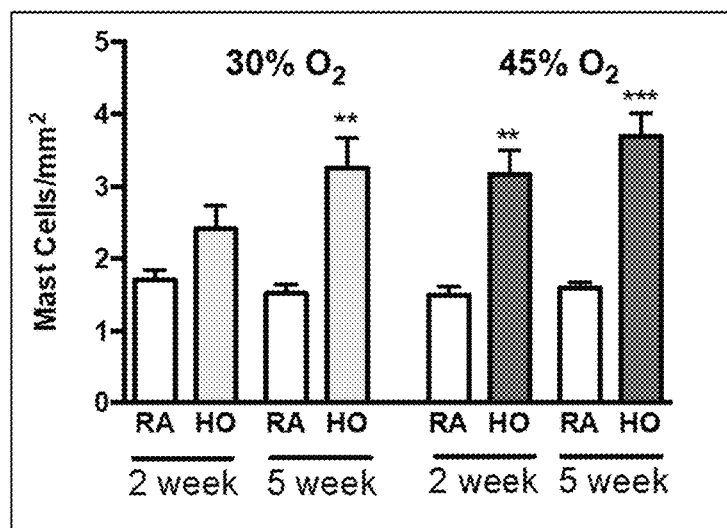
FIG. 11. Mild (30%) and moderate (45%) neonatal hyperoxia (HO) increases lung mast cells. Data are from the 2- and 5-week time points. Comparisons within groups are to the RA mice. P<0.01 and *P<0.001 N=4 mice/group.

Results presented above (FIG. 7) demonstrate that mild (30%) and moderate (45%) hyperoxia cause alveolar simplification and enlargement albeit, not as pronounced as that observed with severe hyperoxia (80%). Likewise, the number of mast cells is significantly increased following mild (30%) and moderate (45%) neonatal oxygen levels compared to the room air timed controls (FIG. 11). Collectively, these data show that even moderate and mild neonatal hyperoxia lead to a persistent increase in lung mast cells and an impaired alveolar phenotype. These results support the experimental design used herein to use clinically relevant oxygen levels.

Figures 12A, 12B:
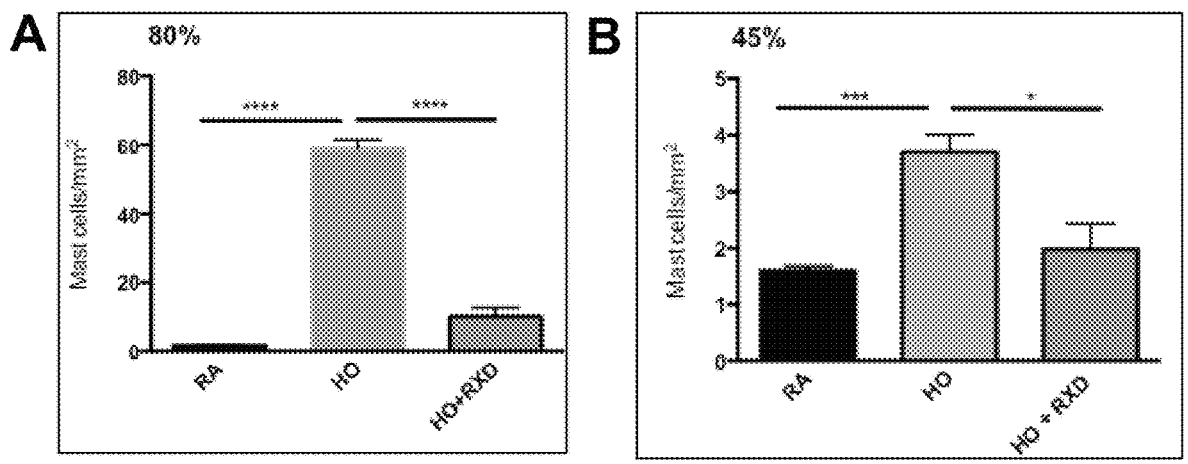
FIG. 12A-12B. HIF stabilization inhibits neonatal hyperoxia-induced increases in lung mast cells. Data are from 5-week time point. RA=room air control; HO=high oxygen; RXD=Roxadustat. (A) Quantification of mast cell number per mm$^2$ of lung tissue under high oxygen levels (80%) with or without RXD treatment compared to RA control. (B) Quantification of mast cell number per mm$^2$ of lung tissue in under moderate oxygen levels (45%) with or without RXD treatment compared to RA control. **P<0.0001; *P<0.001 between RA and HO; *P<0.05 and **P<0.01 between HO and HO+RXD. N=3 mice/group FIG. 13. Mast cells regulate HIF in response to ambient oxygen levels or HIF stabilization. Hypoxia (1% $O_2$, $CoCl_2$), Room air (RA), High oxygen (HO) (80%), RXD=roxadustat. Mast cells were exposed for 24 hours in each condition and their lysate probed by Western blotting.

Example 8: HIF Stabilization Inhibits the Increase in Mast Cells in Response to Neonatal Hyperoxia A screen of fixed lung tissue from RA and HO mice stained for mast cells shows that treatment with a PHDi (10 mg/kg Roxadustat=RXD) prevents the increase in mast cells associated with neonatal hyperoxia. This was observed in both severe (80%) (FIG. 12A) and moderate (45%) hyperoxia (FIG. 12B). This finding points to a means by which PHDi is protective against hyperoxia-induced neonatal lung disease.

Example 9: Mast Cells Regulate HIF in Response to Hypoxia and Hyperoxia

Figure 13:
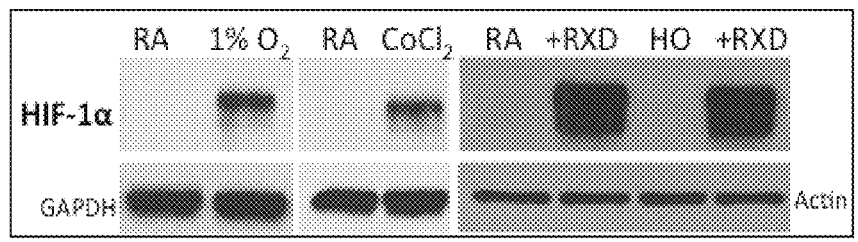

In vitro experiments with the human mastocytoma cell line (HMC-1) confirmed that we could measure HIF in response to hypoxia: 1% $O_2$ and the hypoxia chemical mimetic, cobalt chloride ($CoCl_2$) (FIG. 13). In addition, mast cell HIF was found to be responsive to PHDi in that relative HIF abundance was increased in mast cells maintained in room air+Roxadustat (RA+RXD) and high oxygen+Roxadustat (HO+RXD).

Figure 14:
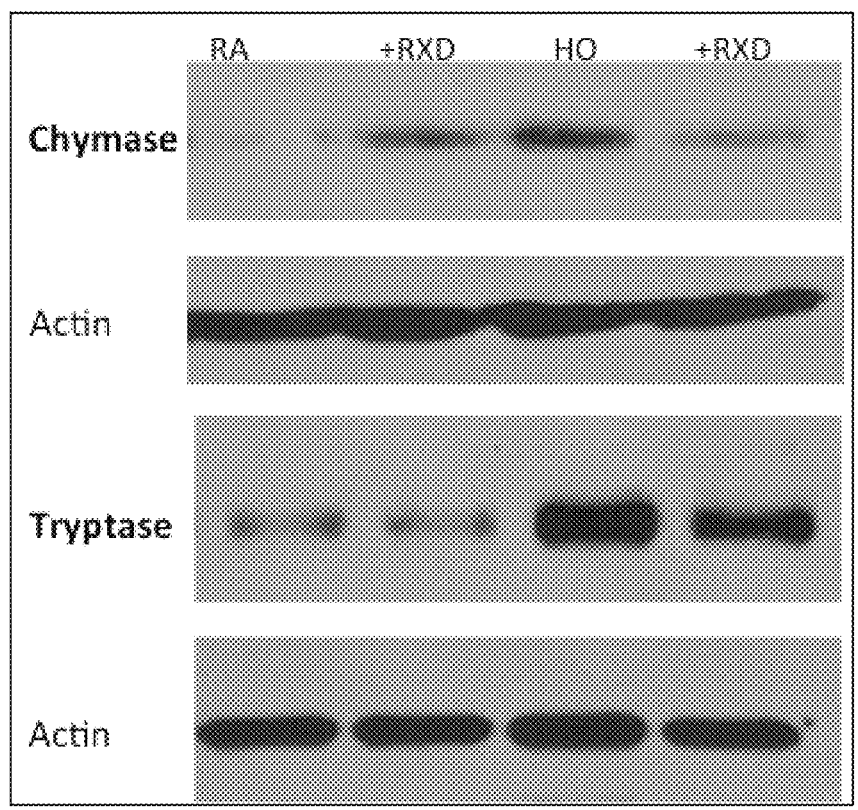
FIG. 14. Roxadustat decreases the relative abundance of hyperoxia-induced mast cell proteases. Mast cells express tryptase and chymase. The relative abundance of the proteases is increased in high oxygen (HO) (80%). Treating with roxadustat (RXD) in the presence of high oxygen decreases the protease abundance. N=4 separate blots, different samples.

Example 10: HIF Stabilization Prevents the Hyperoxia-Induced Upregulation of Mast Cell Proteases Mast cells contain the proteases (tryptase and chymase) that are potentially destructive to the lung. Treatment with RXD decreased the hyperoxia-induced increase in protease abundance (FIG. 14). These results describe a link between mast cells, HIF, and modulation of mast cell mediators.

The data presented herein identifies mast cells as a specific target of HIF stabilizers such as Roxadustat for preventing impaired alveolarization. HIF stabilizers such as Roxadustat protect the neonatal lung from hyperoxia-induced lung damage by preventing the increase in mast cells and downregulating potentially destructive mast cell proteases that lead to irreversible damage.

What is claimed is:

1. A method, comprising administering to a premature newborn who is given oxygen supplementation, a small molecule prolyl hydroxylase domain (PHD) inhibitor in an amount effective to prevent chronic lung disease in the newborn, wherein the PHD inhibitor is administered intermittently beginning at birth and by aerosolized delivery to the lungs of the newborn.

2. The method of claim 1, wherein the PHD inhibitor is administered every other day.

3. The method of claim 1, wherein the PHD inhibitor has the following chemical structure

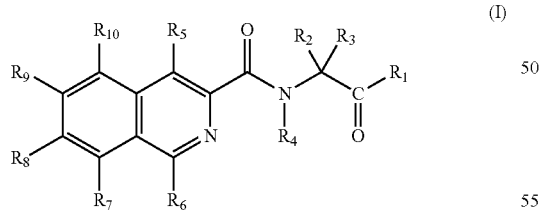

(I)

wherein:

R1 is selected from the group consisting of hydroxyl, alkoxy, substituted alkoxy, aryloxy, and substituted aryloxy;

R2 and R3 are independently selected from the group consisting of hydrogen, alkyl, substituted alkyl, cycloalkyl, substituted cycloalkyl, aryl, substituted aryl, heterocycloalkyl, substituted heterocycloalkyl, heteroaryl, and substituted heteroaryl; or R2 and R3 together with the carbon atom to which they are attached form a cycloalkyl, substituted cycloalkyl, hererocycloalkyl, or substituted hererocycloalkyl;

R4 is selected from the group consisting of hydrogen, alkyl, and substituted alkyl;

R5 is selected from the group consisting of hydroxyl, alkoxy, and substituted alkoxy;

R6 is selected from the group consisting of hydrogen, alkyl, substituted alkyl, cycloalkyl, substituted cycloalkyl, cyano, halo, hydroxyl, alkoxy, substituted alkoxy, amino, substituted amino, arylozy, substituted arylozy, aminoacyl, substituted aminoacyl, cycloalkoxy, substituted cycloalkoxy, aryl, substituted aryl, aryloxy, substituted aryloxy, heterocycloalkyl, substituted heterocycloalkyl, heteroaryloxy, substituted heteroaryloxy, heteroaryl, and substituted heteroaryl; and R7, R8, R9 and R10 are independently selected from the group consisting of hydrogen, halo, alkyl, substituted alkyl, cycloalkyl, substituted cycloalkyl, aryl, substituted aryl, heteroaryl, substituted heteroaryl, alkoxy, substituted alkoxy, aryloxy, and substituted aryloxy.

4. The method of claim 3, wherein said PHD inhibitor is FG-4592.

5. The method of claim 4, wherein said PHD inhibitor is administered in an amount of 0.2 mg/kg to 20 mg/kg.

6. The method of claim 4, wherein said PHD inhibitor is administered only when oxygen is supplemented to said newborn.

7. The method of claim 1, wherein the PHD inhibitor is DMOG.

8. The method of claim 7, wherein said DMOG is administered at an amount between 50 mg/kg and 200 mg/kg.

9. The method of claim 7, wherein said DMOG is administered only when oxygen is supplemented to said newborn.

10. The method of claim 1, wherein the PHD inhibitor is administered until the premature newborn is no longer in need for supplemental oxygen.

11. The method of claim 2, wherein the PHD inhibitor is administered until the premature newborn is no longer in need for supplemental oxygen.

\* \* \* \* \*

SEQUENCE LISTING

<160> NUMBER OF SEQ ID NOS: 16

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide

<400> SEQUENCE: 1
aattgctcct gtccactttg ac                                              22

<210> SEQ ID NO 2
<211> LENGTH: 23
<212> TYPE: DNA
<213> ORGANISM: Artificial Sequence
<220> FEATURE:
<223> OTHER INFORMATION: Oligonucleotide

<400> SEQUENCE: 2
tcactaactc ggaaatccac agt                                             23

<210> SEQ ID NO 3
<211> LENGTH: 21
<212> TYPE: DNA
<213> ORGANISM: Artificial Sequence
<220> FEATURE:
<223> OTHER INFORMATION: Oligonucleotide

<400> SEQUENCE: 3
gccaatgaca cctactggat g                                               21

<210> SEQ ID NO 4
<211> LENGTH: 22
<212> TYPE: DNA
<213> ORGANISM: Artificial Sequence
<220> FEATURE:
<223> OTHER INFORMATION: Oligonucleotide

<400> SEQUENCE: 4
gagctgtact ctgaccttgt tg                                              22

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide

<400> SEQUENCE: 5
ctggctagtc tggtgtactc g                                               21

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide

<400> SEQUENCE: 6
ctggctagtc tggtgtactc g                                               21

<210> SEQ ID NO 7
<211> LENGTH: 17
<212> TYPE: DNA
<213> ORGANISM: Artificial Sequence

```
<220> FEATURE:
<223> OTHER INFORMATION: Oligonucleotide

<400> SEQUENCE: 7
aacagctccc actcttc                                                  17

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide

<400> SEQUENCE: 8
cctgttgctg tagccgtatt                                               20

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide

<400> SEQUENCE: 9
gggtttgatt gctaccactc tt                                            22

<210> SEQ ID NO 10
<211> LENGTH: 23
<212> TYPE: DNA
<213> ORGANISM: Artificial Sequence
<220> FEATURE:
<223> OTHER INFORMATION: Oligonucleotide

<400> SEQUENCE: 10
gccaagtcct ttatgatgtc tgc                                           23

<210> SEQ ID NO 11
<211> LENGTH: 23
<212> TYPE: DNA
<213> ORGANISM: Artificial Sequence
<220> FEATURE:
<223> OTHER INFORMATION: Oligonucleotide

<400> SEQUENCE: 11
gtgacgcaaa ataccacctt ggc                                           23

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide

<400> SEQUENCE: 12
cattcacctt gcacaccagg g                                             21

<210> SEQ ID NO 13
<211> LENGTH: 19
<212> TYPE: DNA
<213> ORGANISM: Artificial Sequence
<220> FEATURE:
<223> OTHER INFORMATION: Oligonucleotide

<400> SEQUENCE: 13
ccgcgaccga tactggatg                                                19
```

```
<210> SEQ ID NO 14
<211> LENGTH: 20
<212> TYPE: DNA
<213> ORGANISM: Artificial Sequence
<220> FEATURE:
<223> OTHER INFORMATION: Oligonucleotide

<400> SEQUENCE: 14
gatctgggcg gtgtagaact                                              20

<210> SEQ ID NO 15
<211> LENGTH: 16
<212> TYPE: DNA
<213> ORGANISM: Artificial Sequence
<220> FEATURE:
<223> OTHER INFORMATION: Oligonucleotide

<400> SEQUENCE: 15
caacagcaca ggagag                                                  16

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide

<400> SEQUENCE: 16
ctacatggca actgtgagga g                                            21
```